US008597910B1

(12) United States Patent
Ginsburg et al.

(10) Patent No.: US 8,597,910 B1
(45) Date of Patent: Dec. 3, 2013

(54) DNA ENCODING VON WILLEBRAND FACTOR (VWF) AND METHODS AND CELLS FOR PRODUCING VFW, AND VFW PRODUCED BY THE DNA, METHODS AND CELLS

(75) Inventors: David Ginsburg, Ann Arbor, MI (US); Stuart H. Orkin, Newton, MA (US); Randal J. Kaufman, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 07/559,509

(22) Filed: Jul. 23, 1990

Related U.S. Application Data

(63) Continuation of application No. 06/882,983, filed as application No. PCT/US86/00760 on Apr. 10, 1986, now abandoned, which is a continuation-in-part of application No. 06/722,108, filed on Apr. 11, 1985, now abandoned.

(51) Int. Cl.
*C12P 21/04* (2006.01)
*C12N 15/00* (2006.01)
*C12N 5/07* (2010.01)
*A61K 35/14* (2006.01)
*C07H 21/04* (2006.01)

(52) U.S. Cl.
USPC ....... 435/69.6; 435/320.1; 435/358; 435/364; 435/365; 530/380; 536/23.5

(58) Field of Classification Search
USPC ......... 435/70, 68, 240.2, 172.3, 6, 69.1, 69.2, 435/69.6, 71.2, 71.1, 91, 172.1, 435/252.3–252.35, 320.1, 240.1; 935/9, 11, 935/12, 32, 58, 60, 70, 10, 76, 77, 71; 536/27; 436/63, 69, 94, 501, 504; 530/383
See application file for complete search history.

(56) References Cited

U.S. PATENT DOCUMENTS

| | | | |
|---|---|---|---|
| 4,386,068 A * | 5/1983 | Mitra et al. | 530/383 |
| 4,423,147 A | 12/1983 | Secher et al. | |
| 4,624,918 A | 11/1986 | Hershberg | |
| 4,670,543 A | 6/1987 | Bourgois et al. | |
| 4,719,177 A | 1/1988 | Baltimore et al. | |
| 4,851,341 A | 7/1989 | Hopp et al. | |
| 5,198,349 A | 3/1993 | Kaufman | |
| 5,250,421 A | 10/1993 | Kaufman et al. | |
| 5,618,789 A | 4/1997 | Capon et al. | |
| 6,271,362 B1 | 8/2001 | Morikawa et al. | |

FOREIGN PATENT DOCUMENTS

| | | | |
|---|---|---|---|
| AU | 4538285 | 1/1986 | |
| EP | 0128018 | 12/1984 | |
| EP | 0169562 | 1/1986 | |
| EP | 0197592 | 10/1986 | |
| EP | 0253870 | 3/1993 | |
| GB | 2079292 | 1/1982 | |
| KR | 1999-0066381 | * | 8/1998 |
| WO | 8501961 | 5/1985 | |
| WO | WO 86/06096 | 10/1986 | |
| WO | 8606745 | 11/1986 | |
| WO | WO 87/02707 | 5/1987 | |
| WO | WO 87/04187 | 7/1987 | |

OTHER PUBLICATIONS

Ginsburg et al., *Science* 228(4706): 1401-1406; Jun. 21, 1985.*
Sadler et al., *Federation Proceedings* 44(4): 1069, abstract—No. 3950; Mar. 5, 1985.*
Lynch et al., *Cell* 41: 49-56; May 1985.*
Sadler et al., *Proc. Natl. Acad. Sci. USA* 82(19): 6394-6398; Oct. 1985.*
Verweij et al.; *Nucleic Acids Res.* 13(13): 4699-4717; Jul. 11, 1985.*
Wagner et al.; *Biol. Abstr.* 79(8): 70, abstract No. 64802; Apr. 15, 1985.*
Lynch et al.; *Proc. Natl. Acad. Sci. USA* 80: 2738-2742; May 1983.*
Chan et al.; *Thromb Haemostasis* 50(4): 835-837; 1983.*
Young et al.; *Proc. Natl. Acad. Sci. USA* 80: 1194-1198; Mar. 1983.*
Bloom et al.; *Nature* 308: 434-435; Jun. 1983.*
Luscalzo, J. and Handin, R.I., 1984, Biochem. 23 :3880.*
"Von Willebrand Factor," Wikipedia.com, accessed May 7, 2012.*
Weiss et al., *Science* 182:1149-1157 (1973).
Stel et al. *Blood* 63:1408-1418 (1984).
Lynch et al. Abstract, *Clinical Research*, vol. 33, No. 2, p. 548A (1985).
Timmons et al., *Proc. Nat'l Acad. Sci.* (USA) 81:4935-4939 (1984).
Verweij et al. *Nucl. Acids Res.* 13:82-89 (1985).
Wood et al., *Nature* 312:330-337 (1984).
Zimmerman et al., in *Progress in Hematology* vol. XIII, pp. 279-309, Brown, ed., (1983).
Fischer, Journal of Thrombosis and Thrombolysis 8(3): 197-205 (1999) (Abstract).
Glover, Gene Cloning, The Mechanics of DNA Manipulation, Chapman and Hall, pp. 188-191 (1984).
Gubler et al., Gene 25: 263-269 (1983.
Helfman et al., Proc. Natl. Acad. Sci. USA 80: 31-35 (1983).

(Continued)

*Primary Examiner* — Bradley L Sisson
(74) *Attorney, Agent, or Firm* — Perkins Coie LLP

(57) ABSTRACT

Von Willebrand's Factor (VWF) is produced using an expression vector that includes: 1) a DNA sequence encoding a functional VWF protein; and 2) regulatory DNA capable of effecting expression of that DNA sequence in a host cell transformed with the vector. Restriction fragment length polymorphisms (RFLP's) associated with the VWF gene are identified and used in a probe for determining the source of a VWF gene in a DNA sample. The gene for VWF is localized to the short arm of human chromosome 12 (12p).

36 Claims, 3 Drawing Sheets

(56) References Cited

OTHER PUBLICATIONS

Itakura et al., Science 209: 1401-1405 (1980).
Maniatis et al., Molecular Cloning, A Laboratory Manual, Cold Spring Harbor Laboratory, Cold Spring Harbor, New York (1982).
Melton et al., Nucleic Acids Res. 12: 7035-7055 (1984).
O'Mahony, Plasma-derived and Biotech Products: What is the Future of Haemophilia Theray?, World Federation of Hemophilia, Occasional Papers Monograph Series No. 1 (1999).
Toole et al., Nature 312: 342-347 (1984).
Verweij et al., The EMBO Journal 6(10): 2885-2890 (1987).
Wagner et al., The Journal of Cell Biology 99: 2123-2130 (1984).
Wyler et al., Experientia 39(6): 665 (1983).
Patent Interference No. 104,200 (*Pannekoek et al.* v. *Ginsburg et al.*), Final Hearing: Jan. 13, 1987 (Paper No. 167).
Baxter's Press Release (Baxter Announces Therapeutic Development Program for First Blood-Free Recombinant von Willebrand Factor) (Dec. 11, 2006).
Cozens et al., Eur. J. Biochem. 112: 443-450 (1980).
Ginsburg et al., U.S. Appl. No. 06/722,108 (Blood Coagulation).
Kaufman et al., U.S. Appl. No. 06/816,031 (Improved Method for Producing VIII:c).
Fischer et a., FEBS Letters 375: 259-262 (1995).
Mannucci et al., Blood 99(2): 450-456 (2002).
Titani et al., Biochemistry 25(11): 3171-3184 (Jun. 1986).
Titani et al., Biochemistry 25(11): 3171-3184 (Jun. 1986) (On-line Abstract).
Turecek et al., Seminars in Thrombosis and Hemostasis 36(5): 510-521 (2010).
Turecek et al., Blood 94:1637-47 (1999).
Verweij et al., Abstract 728 from the Xth International Congress on Thrombosis and Hemostasis, Molecular Cloning of Human Factor VIII—von Willebrand Factor (vWF) cDNA (1985).
Bebbington et al., Trends in Biotechnology 3(12): 314-317 (1985).
Boom et al., Journal of Virology 58(3): 851-859 (1986).
Busby et al., Nature 316: 271-273 (1985).
Choo et al., Science 244: 359-362 (1989).
Ginsburg et al., Clinical Research 33(2): 546(A) (1985).
Gottlieb et al., Proc. Natl. Acad. Sci. USA 83: 2100-2104 (1986).
Graham et al., J. gen. Virol. 36: 59-72 (1977).
Graham et al., J. gen. Virol. 68: 937-940 (1987).
Hacker et al., Biotechnology Advances 27: 1023-1027 (2009).
Hacker et al., Recombinant Protein Production Yields from Mammalian Cells: Past, Present, and Future, BioPharm International, pp. 1-5 (2008).
Horowitz et al., Journal of Molecuar and Applied Genetics 2: 147-159 (1983).
Kaufman et al., Molecular and Cellular Biology 2(11): 1304-1319 (1982).
Kaufman et al., Proc. Natl. Acad. Sci. USA 82: 689-693 (1985).
Kaufman et al., Molecular and Cellular Biology 5(7): 1750-1759 (1985).
Kaufman et al., J. Mol. Biol. 159: 601-621 (1982).
Kelly, Arch Dis Chil. 75(5): 363-365 (1996).
Kuo et al., Science 244: 362-364 (1989).
Luthman et al., Nucleic Acids Research 11(5): 1295-1308 (1983).
Maciag et al., The Journal of Cell Biology 94: 511-520 (1982).
Maciag et al., The Journal of Cell Biology 91: 420-426 (1981).
Messing, Methods in Enzymology 101: 20-78 (1983).
Powell et al., Proc. Natl. Acad. Sci. USA 83: 6465-6469 (1986).
Sanger et al., Proc. Natl. Acad. Sci. USA 74(12): 5463-5467 (1977).
Sompayrac et al., Proc. Natl. Acad. Sci. USA 78(12): 7575-7578 (1981).
Thornton et al., Science 222: 623-625 (1983).
Watson Nucleic, Acids Research 12(13): 5145-5164 (1984).
Wong et al., Science 228: 810-815 (1985).
MMRW 60: 537-541 (2011), published in JAMA 305(24): 2511-2513 (2011).
Guidance for Industry, Draft Guidance for Industry: Amendment to "Guidance for Industry: Revised Preventive Measures to Reduce the Possible Risk of Transmission of Creutzfeldt-Jakob Disease and Variant Creutzfeldt-Jakob Disease by Blood and Blood Products", U.S. Dept. of Health and Human Services, Food and Drug Administration, and Center for Biologics Evluation and Research (2012).
Lusher, American Society of Hematology, Hemophilia: From Plasma to Recombinant Factors, Hematology, downloaded Apr. 23, 2013.
Mason, Mad cow infected blood 'To kill 1,000', The Daily Telegraph (Apr. 29, 2013).

\* cited by examiner

DNA ENCODING VON WILLEBRAND FACTOR (VWF) AND METHODS AND CELLS FOR PRODUCING VFW, AND VFW PRODUCED BY THE DNA, METHODS AND CELLS

This application is a continuation of U.S. application no. 06/882,983, filed Jun. 13, 1986, now abandoned, which is a national stage application of international application PCT/US86/00760, filed Apr. 10, 1986, which is a continuation-in-part of application no. 06/722,108, filed Apr. 11, 1985, now abandoned.

The invention described herein was supported, in whole or in part, by grant RO1HL032259 from the Department of Health and Human Services, National Institutes of Health. The United States Government has certain rights in the invention.

BACKGROUND OF THE INVENTION

This invention relates to mammalian Von Willebrand Factor (VWF), which is also known as Factor VIIIR, and to methods for obtaining and using VWF and for analyzing a mammalian DNA sample for the presence of VWF gene.

Blood coagulation in mammals involves the interaction of a number of protein factors and tissue components. One coagulation factor complex is called Factor VIII and is composed of at least two distinct proteins: Factor VIIIC (antihemophilic factor, the protein that corrects the coagulation disorder known as hemophilia A), and VWF. VWF is a protein that binds to platelets and is an essential component in platelet-vessel wall interaction during the clotting process. Zimmerman et al., *Progress in Hematology* Vol. XIII, "Factor VIII/Von Willebrand Factor", (Grune & Stratton 1983). Diminished or abnormal VWF activity can result in Von Willebrand's Disease (VWD), a relatively common and complex hereditary bleeding disorder. The Factor VIII complex, obtained as a cryoprecipitate from donor blood, is administered as a therapy for VWD. Mitra, U.S. Pat. No. 4,386,068. cDNA's specific for other coagulation proteins, e.g., Factor VIIIC, have been cloned and expressed in host systems [Wood et al (1984) Nature 312:330-3371].

VWF is particularly difficult to analyze and produce because it is very large and there has been very little, if any, sequence data available heretofore. Moreover, cells that produce substantial amounts of VWF, e.g., endothelial cells and megakaryocytes, are difficult to grow in culture.

SUMMARY OF THE INVENTION

One aspect of the invention generally features producing VWF using an expression vector that includes: 1) a DNA sequence encoding a functional mammalian VWF protein; and 2) regulatory DNA capable of effecting expression of that DNA sequence in a host cell transformed with the vector. By a functional mammalian VWF protein we mean a protein that corresponds sufficiently to a naturally occurring mammalian VWF protein to have or to be processed to have the function of a naturally occurring Von Willebrand factor; processing may include glycosylation and/or assembly into multimers. By a host cell we mean any suitable host cell such as a mammalian cell. At least some of the expression vector is exogenous to the VWF-encoding DNA sequence, meaning that it does not naturally occur in the same molecule with that sequence.

In preferred embodiments, the VWF is human VWF, and the host cell for producing the functional VWF is a eukaryotic cell, most preferably a mammalian cell.

A second aspect of the invention generally features analyzing a mammalian DNA sample using a probe comprising DNA encoding a VWF protein, or a fragment thereof, labeled with a detectable label. The probe is contacted with the sample to determine whether it hybridizes with the sample.

In a third aspect, the mammalian DNA that is to be analyzed is fragmented using restriction enzyme digestion, the DNA fragments are separated on the basis of size, the fragments are contacted with the above described probe, and the relative lengths of the DNA fragments that hybridize to the probe are determined.

In preferred embodiments of both the second and third aspects, both the probe and the DNA being analyzed are human DNA.

The invention thus provides a relatively plentiful and pure source of VWF for treating bleeding disorders, for example, by administering: VWF to those with VWD; VWF in a stable complex with factor VIIIC to those with hemophilia A; or VWF to those with bleeding disorders associated with renal failure. The invention also provides diagnostic and research tools for evaluating VWF genes and defects in them using labeled probes comprising the VWF gene or fragments of it. For example, a mammalian DNA sample can be analyzed using a DNA probe to detect a restriction fragment length polymorphism (RFLP) specifically associated with that VWF-related gene. By a VWF-related gene, we mean a normal VWF gene, or DNA characterized by the absence of part or all of the VWF gene or by a mutant VWF gene. Restriction fragment length polymorphism means an identifiable DNA sequence that is associated with the VWF-related gene and is conserved together with the VWF-related gene. RFLP's can be used to determine the pattern of inheritance of VWF genes, e.g. in a fetus at risk for one of the various forms of VWD. Other features and advantages of the invention will be apparent from the following descriptions of the preferred embodiments and from the claims.

DESCRIPTION OF THE PREFERRED EMBODIMENT

We now describe preferred embodiments of the invention, first briefly describing the drawings.

I. Drawings

II. Structure and Use

Figure 1A:
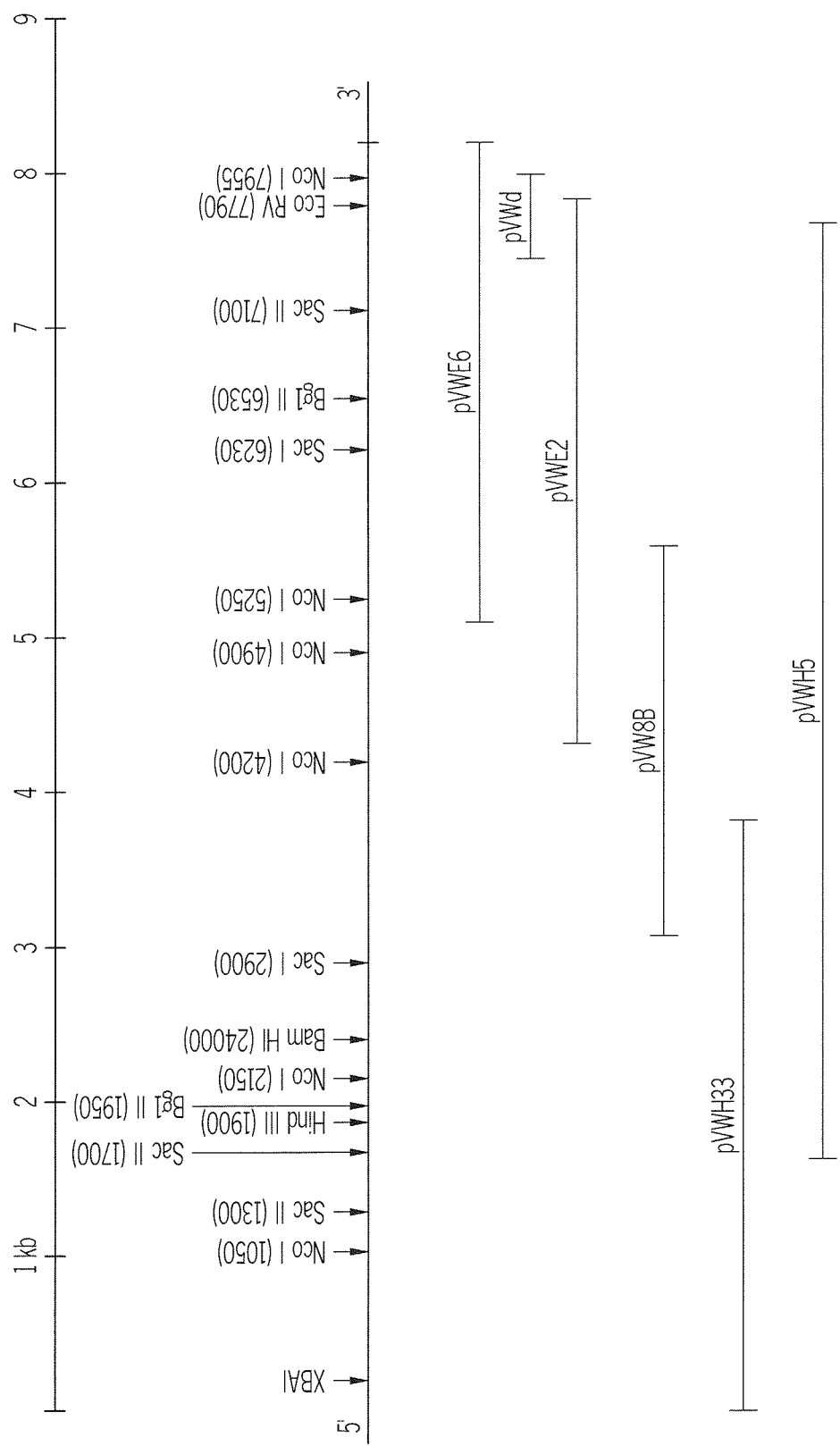
FIG. 1A represents a restriction map of VWF DNA.

Section A below describes how to make functional human VWF by first assembling cDNA fragments to yield a cDNA coding for a functional human VWF protein and then expressing that cDNA in a host cell.

Section B describes the use of cDNA encoding VWF protein to analyze sample DNA, e.g., by detecting restriction fragment length polymorphisms (RFLP's) that are associated with the human gene. An assay can then be performed to determine the source of a VWF gene in a human DNA sample—e.g. which allele of each parent was inherited.

A. Functional VWF Protein

The process of making functional VWF protein involves: A) obtaining human mRNA; B) making a cDNA library from that mRNA and identifying cDNA fragments coding for VWF; C) assembling those fragments into a cDNA molecule encoding a functional VWF protein; and D) producing VWF by cloning that cDNA molecule into an expression vector that can be used to transform a eukaryotic host cell.

1. Obtaining the mRNA

As a source of VWF mRNA, a primary culture of human umbilical vein endothelial cells (HUVEC) is grown and passaged in cell culture in Medium 199 with 20% fetal bovine serum in the presence of bovine endothelial cell growth factor and fibronectin according to the method of Maciag et. al. (J. Cell Biol. 91:420-426 (1981), J. Cell Biol. 94:511-520 (1982)]. Growth is markedly enhanced by the addition of heparin as described by Thornton et al. [Science 222: 623-625 (1983)]. To verify the presence of VWF mRNA, both the cultured cells and the conditioned medium are tested for the presence of VWF using anti-VWF antibody obtained by standard techniques. Standard immunofluorescense and ELISA assay, respectively, can be used for this purpose. After four additional passages, cells are harvested and total RNA prepared in guanidine HCl by standard techniques.

2. Constructing a cDNA Library

Poly-A$^+$ mRNA is isolated from total endothelial cell RNA by oligo-dT cellulose column chromatography. Two cDNA pools for the preparation of two different cDNA libraries are synthesized from the mRNA using standard techniques. For the first cDNA pool, oligo-dT is used as primer for the first strand synthesis, whereas for the second cDNA pool random oligonucleotide is used as primer for the first strand. The cDNA pools are made blunt-ended by treatment with T4 DNA polymerase and ligated to EcoRI linkers with T4 DNA ligase after protection of internal EcoRI sites by treatment with E. coli methylase. The linker-ligated cDNA's are then digested with an excess of EcoRI restriction enzyme and separated from free linkers by passage over a Sepharose CL4B column.

The phage vector selected for carrying the VWF cDNA into a bacterial host is lambda gt11, a derivative of bacteriophage lambda which contains a bacterial gene for beta-galactosidase with a single EcoRI cloning site located near its 3' end, corresponding to the C-terminal portion of the beta-galactosidase protein. cDNA molecules are inserted into this site to construct a cDNA library.

By infecting an appropriate strain of bacteria with this phage using known techniques, a fusion protein will be produced containing most of beta-galactosidase at its aminoterminus and a peptide fragment of the protein of interest at the carboxy-terminus. If this cDNA-encoded peptide contains one of the antigenic determinants of VWF, it is detected by screening with anti-VWF antibody. Large numbers of phage particles can be grown on a bacterial plate and the protein products transferred to a nitrocellulose filter and screened with a specific antibody to identify the location of the recombinant plaque producing the protein of interest.

Specifically, the VWF cDNA is ligated into EcoRI digested, phosphatase treated lambda gt11 vector DNA and two libraries containing between 3–4×10$^6$ recombinant clones each are plated and amplified. Nonrecombinant background as assessed by growth on ITPG/XGa1 plates is approximately 30%. Recombinant clones are obtained having cDNA inserts ranging in size from approximately 1 to 3 kilobases (kb) in length.

Affinity purified rabbit heteroantiserum prepared against human factor VIII-VWF is obtained using standard methods. The antiserum is passed over gelatin-sepharose, and adsorbed and eluted from a column of VWF-sepharose.

Recombinant clones from the above lambda-gtII endothelial cell cDNA libraries are screened as phage plaques in E. coli host strain Y1090 with this antibody at a 1:1000 dilution. Potential positive plaques are purified, replated and rescreened. For example, one primary filter screened with anti-human VWF antibody showed a positive plaque designated LVWd. As a positive control, purified VWF protein can be spotted onto the filter and can be detected at amounts between 100 and 0.1 nanograms (ng) total protein.

Positive plaques from the rescreening are purified and phage DNA prepared by standard methods. Purification and characterization of the cDNA insert in the above-described LVWd plaque are described below.

The 553 bp cDNA insert of LVWd is purified by agarose gel electrophoresis following EcoRI digestion and used as a probe to examine Northern blots of total mRNA from endothelial cells prepared as described above. Northern blot analysis was performed on total cell RNA from HPB-ALL (a T-cell line), endothelial cells (HUVEC), fibroblasts, and Hela cells, with the LVWd cDNA insert as the hybridization probe. The LVWd cDNA probe hybridized with a single mRNA band between 8 and 10 kb in length. This mRNA species is large enough to code for a protein on the order of 250K dalton in molecular weight. This mRNA species was detected only in endothelial cells; no hybridization was observed with RNA's from the controls, i.e., human fibroblasts, Hela cells, or a human T-cell line (HPB-ALL). Thus the cDNA insert of clone LVWd corresponds to a segment of an mRNA molecule that is present only in endothelial cells and that is large enough to code for VWF. The clone contains a polypeptide epitope which reacts with affinity purified anti-VWF antibody.

Figure 1B:
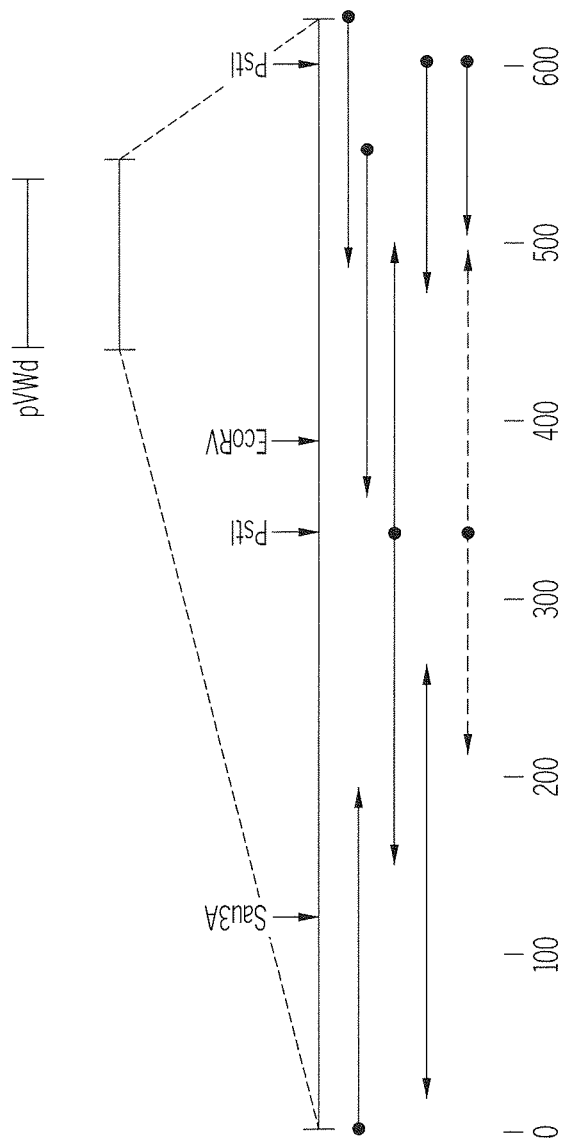
FIG. 1B represents a restriction map of the 3' portion of VWF cDNA derived from a plasmid designated pVWd and the 3' end of the overlapping clone pVWE6.
Figure 2:
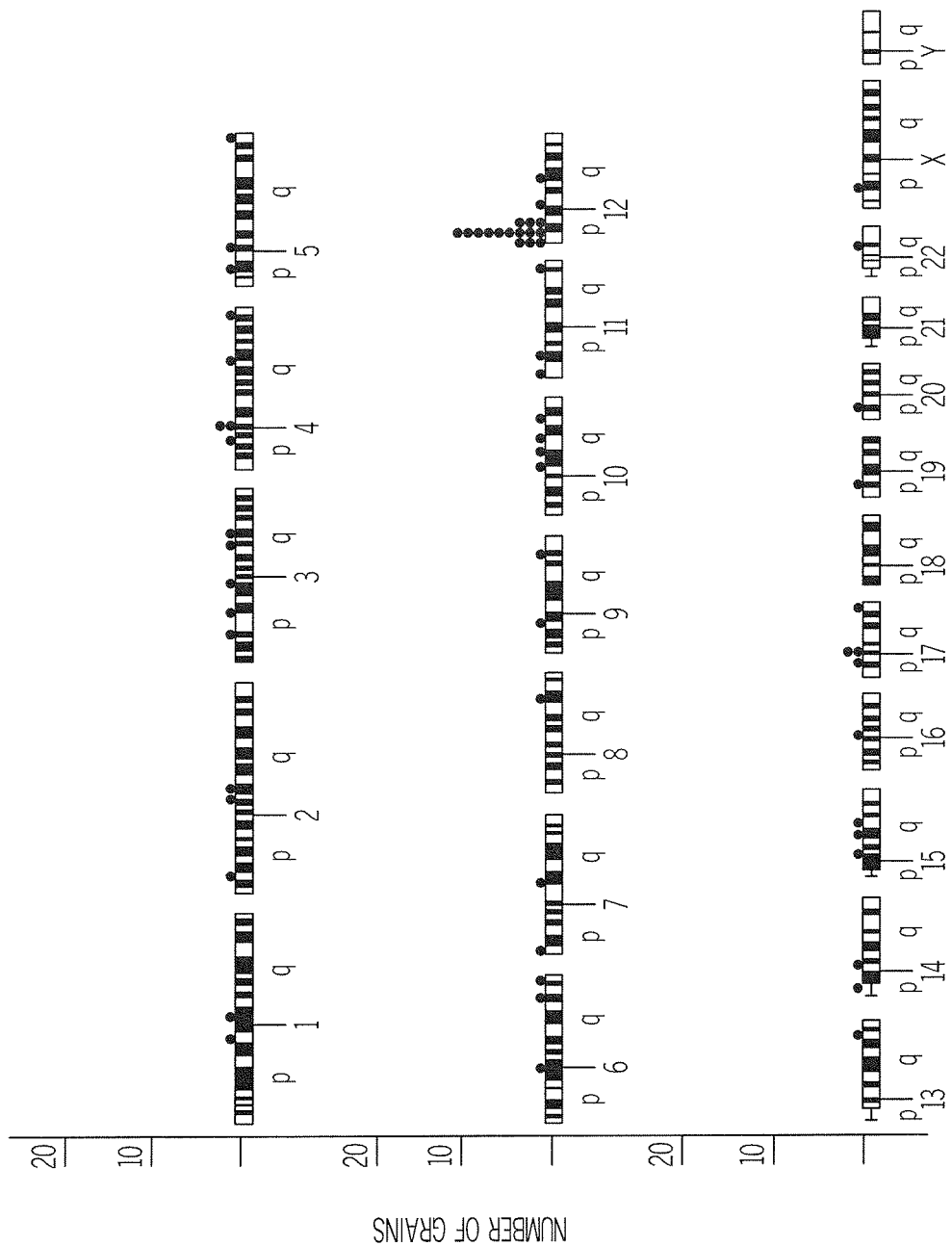
FIG. 2 is a diagram of the chromosomal localization for the human VWF gene as determined by in situ hybridization.

The cDNA insert of LVWd is subcloned into plasmid pUC-13 (P-L Biochemicals) yielding the plasmid pVWd. FIG. 1A is a restriction map of cDNA coding for a VWF protein. FIG. 1B represents a restriction fragment map and sequencing strategy for DNA from the 3' portion of VWF cDNA derived from pVWd and the 3' end of the overlapping clone pVWE6 (see FIG. 1A). In both FIG. 1A and FIG. 1B, the DNA segment designated pVWD is the above-described cDNA fragment of the plasmid pVWD. Solid lines and arrows in FIG. 1B indicate regions sequenced by the method of Maxam and Gilbert [Meth. Enzymol. 65:499-560 (1980)], with the solid circles indicating the end labeled restriction site. Dotted lines and arrows indicate regions sequenced by the method of Sanger et al., [Proc. Natl. Acad. Sci. USA 74: 5463-4567 (1977)] using PstI fragments subcloned into M13 mpII.

Table 1 shows the DNA sequence of the cDNA fragment of FIG. 1B. The cDNA sequence contains a single large open reading frame encoding 193 amino acids followed by a single in the same reading frame and orientation as the beta-galatosidase gene with which it was fused, consistent with expression of a fusion protein product. The predicted amino acid sequence for 193 amino acid residues at the carboxy-terminus of VWF is also shown using the standard single letter amino acid code. The six nucleotides at the beginning and at the end of the DNA sequence correspond to the synthetic EcoRI linker introduced by the cloning procedure. The single termination codon is marked by a diamond. Arrowheads indicate two potential N-glycosylation sites.

The chromosomal assignment of the VWF gene is established by the use of cDNA obtained as described above. FIG.

2 represents the hybridization patterns which indicate the localization of the VWF gene to the short arm of chromosome 12 (12p).

The following biological materials have been deposited with the American Type Culture Collection ("ATCC"), P.O. Box 1549, Manassas, Va. 20108: pVWH5, deposited Apr. 10, 1985, accession no. 53088; LVWd, deposited Apr. 10, 1985, accession no. 53089; pVWH33, deposited Apr. 10, 1985, accession no. 53090; and pVWE6, deposited Aug. 8, 1989, accession no. 40643.

3. Assembling cDNA Fragments

In order to build a cDNA segment corresponding to a VWF protein, an insert from a positive plaque such as the 553 base pair insert of LVWd is used as a probe to rescreen the above-described HUVEC libraries, and to produce the restriction map of VWF cDNA shown in FIG. 1A.

Specifically, the cDNA insert is purified in low melt agarose (Bethesda Research Labs) following EcoRI digestion,

TABLE 1

```
                        10           20           30           40           50           60
                         *            *            *            *            *            *
            AA TTC CGG AAG ACC ACC TGC AAC CCC TGC CCC CTG GGT TAC AAG GAA GAA AAT AAC ACA GGT
                       K   T   T   C   N   P   C   P   L   G   Y   K   E   E   N   N   T   G
                                                                               ▲

70           80           90          100          110          120
                         *            *            *            *            *            *
            GAA TGT TGT GGG AGA TGT TTG CCT ACG GCT TGC ACC ATT CAG CTA AGA GGA GGA CAG ATC
             E   C   C   G   R   C   L   P   T   A   C   T   I   Q   L   R   G   G   Q   I 130          140          150          160          170          180
                         *            *            *            *            *            *
            ATG ACA CTG AAG CGT GAT GAG ACG CTC CAG GAT GGC TGT GAT ACT CAC TTC TGC AAG GTC
             M   T   L   K   R   D   E   T   L   Q   D   G   C   D   T   H   F   C   K   V 190          200          210          220          230          240
                         *            *            *            *            *            *
            AAT GAG AGA GGA GAG TAC TTC TGG GAG AAG AGG GTC ACA GGC TGC CCA CCC TTT GAT GAA
             N   E   R   G   E   Y   F   W   E   K   R   V   T   G   C   P   P   F   D   E 250          260          270          280          290          300
                         *            *            *            *            *            *
            CAC AAG TGT CTG GCT GAG GGA GGT AAA ATT ATG AAA ATT CCA GGC ACC TGC TGT GAC ACA
             H   K   C   L   A   G   G   I   M   E   M   K   I   P   G   T   C   C   D   T 310          320          330          340          350          360
                         *            *            *            *            *            *
            TGT GAG GAG CCT GAG TGC AAC GAC ATC ACT GCC AGG CTG CAG TAT GTC AAG GTG GGA AGC
             C   E   E   P   E   C   N   D   I   T   A   R   L   Q   Y   V   K   V   G   S 370          380          390          400          410          420
                         *            *            *            *            *            *
            TGT AAG TCT GAA GTA GAG GTG GAT ATC CAC TAC TGC CAG GGC AAA TGT GCC AGC AAA GCC
             C   K   S   E   V   E   V   D   I   H   Y   C   Q   G   K   C   A   S   K   A 430          440          450          460          470          480
                         *            *            *            *            *            *
            ATG TAC TCC ATT GAC ATC AAC GAT GTG CAG GAC CAG TGC TCC TGC TGC TCT CCG ACA CCG
             M   Y   S   I   D   I   N   D   V   Q   D   Q   C   S   C   C   S   P   T   R 490          500          510          520          530          540
                         *            *            *            *            *            *
            ACG GAG CCC ATG CAG GTG GCC CTG CAC TGC ACC AAT GGC TCT GTT GTG TAC CAT GAT GTT
             T   E   P   M   Q   V   A   L   H   C   T   N   G   S   V   V   Y   H   E   V
                                                                 ▲

550          560          570          580          590          600
                         *            *            *            *            *            *
            CTC AAT GCC ATG GAG TGC AAA TGC TCC CCC AGG AAG TGC AGC AAG TGA GGC TGC TGC AGC
             L   N   A   M   E   C   K   C   S   P   R   K   C   S   K   ◆

610          620          630
                         *            *            *
            TGC ATG GGT GCC TGC TGC TGC CGG AAT T
``` and subcloned into the EcoRI digested and phosphatased pUC-13 plasmid (P-L Biochemicals) to yield pVWD (see FIG. 1A). The EcoRI insert is radiolabeled and used as a probe to rescreen the HUVEC cDNA library. The positive recombinant phage are purified and subcloned into pUC-13. Two such recombinants, pVWE2 and pVWE6, are illustrated in FIG. 1A. The restriction map is deduced by standard methods. A 217 bp EcoRI/PstI fragment from the 5' end of pVWE2 is used to rescreen the HUVEC cDNA library and a third series of overlapping VWF cDNA clones is identified, one of which, pVWG8b, is shown in FIG. 1A. Using the same methods, a fourth series of overlapping clones is obtained, including pVWH33 and pVWH5 which, together with the sequence shown in Table 1, span DNA sufficient to encode an entire monomer of human VWF protein. By using the appropriate restriction enzymes, reagents, and procedures, one skilled in the art can ligate together cDNA fragments of pVWH33, pVWH5, and the sequence of Table 1, for example, to construct a cDNA encoding an entire monomer of VWF protein.

Construction and Expression of Full-Length cDNA

More specifically, cDNA clones pVWH33, pVWH5 and pVWE6, which span 9 kb pairs of DNA and encompass the entire protein coding region of VWF, were selected to construct full length cDNA. Nucleotide sequence of the ends of these clones confirmed that together they include the translational start, protein coding and translational stop sequences. The full length cDNA was constructed by standard techniques using fragments derived from individual clones. A fragment of pVWH33 from the left hand EcoRI site to the unique BamHI site was linked to a pVWH5 fragment from the BamHI site to the Sac II site. This was then linked to a fragment from pVWE6 from the Sac II site to the right hand EcoRI site. The full-length cDNA was then inserted as an EcoRI fragment into the EcoRI site of the expression vector pMT2 in which transcription occurs under the control of the adenovirus major late promoter.

pMT2 is a derivative of the mammalian cell expression vector p91023(B) (Wong et al., Science 228: 810-815 (1985)) in which the tetracycline resistance marker is substituted for the ampicillin resistance marker. The functional elements of the VWF expression plasmid have been previously described (Kaufman, Proc. Natl. Acad. Sci. USA 82 :689-693 (1985)). pMT2-VWF contains the SV40 origin and enhancer element; the adenovirus major late promoter with the first, second and two thirds of the third tripartite leader; an intron from the 5' splice site from the first late leader of adenovirus and 3' splice site from an immunoglobulin gene (Kaufman & Sharp '82); the VWF cDNA; DHFR coding region, and SV40 early polyadenylation site; the adenovirus VA genes in a derivative of pBR322 containing the Col E1 origin of replication and ampicillin resistance.

pMT2-VWF was grown in E. coli DH5 in order to prevent deletion of the VWF sequence. Plasmid DNA was prepared by twice banding to equilibrium on CsCl gradients.

4. Production and Use of VWF

The above-described cDNA encoding a VWF protein can be inserted into a suitable vector and expressed in any one of a number of mammalian expression systems known to the art, for example using the general method described by Wood et al. (1984) Nature 312:330-337. The resulting product with any necessary post-translational processing, yields a mature Von Willebrand factor. Host systems can be selected for appropriate post translational processing of the VWF gene product, and enable efficient recovery of VWF. Active VWF has thus been expressed in COS monkey cells and in CHO cells, for example, as described below. Pure VWF produced in this way will be useful in the treatment of VWD, and patients with chronic renal failure whose abnormal bleeding times are corrected by crude cryoprecipitate. Pure VWF can also be used to carry, stabilize, and improve the therapeutic efficacy of factor VIII:C.

Expression of VWF in Monkey COS Cells.

The SV40-transformed COS monkey cells (clone M6) have been described (Horowitz et al., 1983, J. Mol. Appl. Genet. 2: 147-149). DNA transfections using pMT2 and pMT2-VWF were performed as described (Kaufman, Proc. Natl. Acad. Sci. USA 82 :689-693 (1985)) by the DEAE-dextran procedure with the addition of a chloroquin treatment Sompayrac et al., Proc. Natl. Acad. Sci. 78: 7575-7578 (1981); Luthman et al., Nucl. Acids Res. 11: 1295-1308 (1983)). Transfected cells were fed with DMEM (Dulbecco's Modified Eagle's Media) with 10% total bovine serum for 48 hr. Then the media was removed, the cells rinsed, and serum-free DMEM applied (4 ml per $3\times10^6$ cells) for measurement for VWF using an inhibition ELISA assay in which purified VWF was adsorbed onto the surface of microtiter wells followed by anti-VWF antibody. The ability of test material to displace anti-VWF antibody from the immobilized antigen was tested using peroxidase conjugated anti-rabbit IgG as the indicator substance. Media from COS cells transfected with expression vector pMT2-VWF containing VWF cDNA produced between 50 and 300 ng/ml VWF antigen in three separate transfections. COS cells transfected with vector pMT2 alone did not produce any protein reacting in the ELISA assay.

Processing of Recombinant VWF

A transfection of COS cells was performed as above and 72 hours post-transfection, the media was replaced with fresh cysteine-free media containing $^{35}$S-cysteine. After an additional 1 to 5 hours of incubation, the media was removed and cell extracts were prepared as described Kaufman et al., J. Mol. Biol. 159: 601-621 (1982). The cell extracts and media were then used for studies of VWF processing and multimer assembly. VWF was immunoprecipitated by incubation with rabbit anti-human VWF antibody, followed by protein-A sepharose. The immunoprecipitated material was washed in a buffer containing 0.1% SDS and NONIDET™ P40 (octyl phenoxy polyethoxyethanol) to minimize non-specific adsorption of other proteins to the immune complex. The precipitated proteins were then analyzed by 4 to 6% SDS-PAGE in the presence and absence of 1 mM DTT. Recombinant cell lysates contained a band migrating with an apparent molecular weight of 260 kd. Cell media contained a mixture of 260 kd and 220 kd species. Immunoprecipitates derived from COS cells or media transfected with non-recombinant plasmid did not contain these two bands. Analysis of non-reduced species by 4% SDS-PAGE showed a series of four or five very high molecular weight proteins varying from 1 to 3 or 4 million daltons.

Biological Activity of Recombinant VWF

COS cells were transfected as above and 48 hr. post-transfection were rinsed and fed with serum free media. Two hundred ml of serum free COS cell media was collected after incubation with COS cells for 24 hours. It contained between 50 and 200 ng/ml VWF by ELISA. The serum free media was concentrated by dialysis against 50% Ficoll to a concentration of 2.2 ug/ml VWF protein for use in the competitive binding assays.

This recombinant VWF was used in varying concentrations as a competing ligand against purified, radiolabelled human VWF multimers in assays as described by Loscalzo et al., Biochem. 23: 3880-3886 (1984). A concentration of 1 ug/ml competed for 50% of the collagen binding (I.C. 50). This was ten fold less than the I.C. 50 when purified human VWF was used as competing ligand. COS media from cells transfected with pMT2 plasmid alone did not compete for collagen binding sites. Similarly, the I.C. 50 for recombinant VWF binding to platelet glycoprotein Ib was 2 ug/ml when using freshly isolated platelets, and 5 ug/ml when using formalin fixed platelets as the source of receptor. These values are identical to those obtained with purified human VWF. Again, media form COS cells transfected with nonrecombinant plasmid did not compete for binding. These results demonstrate that COS cell derived VWF is functional as determined by collagen and platelet binding.

VWF Expression in CHO Cells

Although a number of systems are available for the production of VWF in mammalian cells, one particularly useful approach to obtain high level expression is to select for cells that contain a high degree of amplification of the heterologous VWF gene. One amplifiable marker which is available for this approach is the dihydrofolate reductase gene for which cells harbouring increased gene copies can be selected by propagation in increasing concentrations of methotrexate (MTX) Kaufman et al., J. Mol. Biol. 159: 601-621 (1982). This approach can be used to select and amplify the VWF gene in a variety of different cell types and has been used to obtain expression of active, full-length human VWF in Chinese hamster ovary cells.

Coamplification and Coexpression of VWF and DHFR in DHFR Deficient Chinese Hamster Ovary (CHO) Cells The VWF expression plasmid pMT2-VWF and the DHFR expression plasmid pAdD26SV (A) 3 (Kaufman et al., Mol. Cell, Biol 2: 1304-1319 (1982)) were introduced into DHFR deficient CHO DUKX-BII cells by calcium-phosphate coprecipitation and transfection. DHFR+ transformants were selected for growth in alpha media with dialyzed fetal calf serum and subsequently selected for amplification by growth in increasing concentrations of MTX (sequential steps in 0.02, 0.2, 1.0, and 5.0 uM) as (Kaufman et al., Mol. Cell. Biol. 5: 1750-1759 (1985)). One transformant, designated XMTVWF-C1, was isolated in alpha media and propagated in MTX as described above. The expression of VWF, monitored by ELISA, as a function of increasing levels of MTX resistance is shown below.

| uM [MTX] | ng/ml/day |
|---|---|
| 0.2 | 56 |
| 1.0 | 91 |
| 5.0 | 278 |

VWF expression increased with increasing levels of MTX resistance.

The VWF derived from the CHO cells was assayed by a direct ELISA assay using a rabbit anti-human VWF antibody (Calbiochem) immobilized on microtiter plates and a secondary antibody conjugated to horse radish peroxidase (Dacco). There was minimal activity in the media from the original CHO cells (less than 5 ng/ml). Values were determined by comparison to a standard derived from normal human pooled plasma (1 unit/ml) which was assumed to contain 10 µg/ml of VWF. VWF expression has also been verified by $^{35}$S-cysteine labeling of the cells and analysis of the conditioned media and cell extracts by immunoprecipitation with rabbit anti-human-VWF antisera (Calbiochem) and electrophoresis of SDS-polyacrylamide gels as described above for the VWF derived from transfected COS cells.

5. Nucleotide Sequence of VWF rDNA

The VWF DNA sequence was derived from the same overlapping cDNA clones which were used in the construction of the full-length expressed clone pMT2-VWF. An additional 70 bp of 5' untranslated region, derived from the most 5' clone isolated, pVWK7, has been included. The entire sequence was determined on both strands using the Sanger dideoxy method on single-stranded M13 subclones (Sanger et al., Proc. Natl. Acad. Sci. U.S.A. 74: 5463-5467 (1977); Messing, J. Methods Enzymol. 101: 20-78 (1983)). Sub-clones for sequencing were generated by exonuclease digestion of the inserts of cDNA clones pVWH33, pVWH5, and pVWE2, using nuclease Bal31 or T4 DNA polymerase. Gaps were completed by subcloning appropriate restriction fragments from the same clones into M13 mp10 and mp11.

The sequence of 8588 base pairs is shown in Table 2. It contains continuous open reading frame encoding a polypeptide of 2815 amino acids.

There are three lines of evidence supporting the authenticity of the indicated translational start site. First, there is an upstream nonsense codon in the major open reading frame. Second, the only other upstream start codon is followed almost immediately by an in frame stop codon. Finally, the presumptive initiator methionine is followed by a classical signal peptide sequence, as expected from this secreted glycoprotein.

In order to characterize the 5' untranslated region, several other clones containing the 5' segments of the VWF cDNA partially sequenced but no two independent clones were found to have the same 5' end. As shown here pWK7 extended the farthest 5'.

The apparent discrepancy between the length needed to encode an estimated 260 kd VWF precursor (about 7 kb) and the observed VWF message size of 8-9 kb has been previously noted, and has led some investigators to postulate the presence of an extremely long 5' untranslated region (Lynch et al., Cell 41: 49-56 (1985)). The presence of an 8.3 kb continuous open reading frame clearly shows that the primary VWF transcript is much larger than the 260 kd suggested by SDS-PAGE. The predicted molecular weight is approximately

TABLE 2

| LVWF cDNA sequence with deduced amino acid sequence | | | | | | |
|---|---|---|---|---|---|---|
| 10 | 20 | 30 | 40 | 50 | 60 | 70 |
| GAATTCCGCA | GCTGAGAGCA | TGGCCTAGGG | TGGGCGGCAC | CATTGTCCAG | CAGCTGAGTT | TCCCAGGGAC |
| 80 | 90 | 100 | | 121 | | |
| CTTGGAGATA | GCCGCAGCCC | TCATTTGCAG | GGGAAG ATG | ATT CCT GCC AGA TTT GCC GGG | | |
| | | | M | I P A R F A G | | |

TABLE 2-continued

LVWF cDNA sequence with deduced amino acid sequence

```
    136                 151                 166                 181
GTG CTG CTT GCT CTG GCC CTC ATT TTG CCA GGG ACC CTT TGT GCA GAA GGA ACT
 V   L   L   A   L   A   L   I   L   P   G   T   L   C   A   E   G   T 196                 211                 226
CGC GGC AGG TCA TCC ACG GCC CGA TGC AGC CTT TTC GGA AGT GAC TTC GTC AAC
 R   G   R   S   S   T   A   R   C   S   L   F   G   S   D   F   V   N 241                 256                 271                 286
ACC TTT GAT GGG AGC ATG TAC AGC TTT GCG GGA TAC TGC AGT TAC CTC CTG GCA
 T   F   D   G   S   M   Y   S   F   A   G   Y   C   S   Y   L   L   A 301                 316                 331                 346
GGG GGC TGC CAG AAA CGC TCC TTC TCG ATT ATT GGG GAC TTC CAG AAT GGC AAG
 G   G   C   Q   K   R   S   F   S   I   I   G   D   F   Q   N   G   K 361                 376                 391
AGA GTG AGC CTC TCC GTG TAT CTT GGG GAA TTT TTT GAC ATC CAT TTG TTT GTC
 R   V   S   L   S   V   Y   L   G   E   F   F   D   I   H   L   F   V 406                 421                 436                 451
AAT GGT ACC GTG ACA CAG GGG GAC CAA AGA GTC TCC ATG CCC TAT GCC TCC AAA
 N   G   T   V   T   Q   G   D   Q   R   V   S   M   P   Y   A   S   K 466                 481                 496
GGG CTG TAT CTA GAA ACT GAG GCT GGG TAC TAC AAG CTG TCC GGT GAG GCC TAT
 G   L   Y   L   E   T   E   A   G   Y   Y   K   L   S   G   E   A   Y 511                 526                 541                 556
GGC TTT GTG GCC AGG ATC GAT GGC AGC GGC AAC TTT CAA GTC CTG CTG TCA GAC
 G   F   V   A   R   I   D   G   S   G   N   F   Q   V   L   L   S   D 571                 586                 601                 616
AGA TAC TTC AAC AAG ACC TGC GGG CTG TGT GGC AAC TTT AAC ATC TTT GCT GAA
 R   Y   F   N   K   T   C   G   L   C   G   N   F   N   I   F   A   E

GAT GAC TTT ATG ACC CAA GAA GGG ACC TTG ACC TCG GAC CCT TAT GAC TTT GCC
 D   D   F   M   T   Q   E   G   T   L   T   S   D   P   Y   D   F   A 676                 691                 706                 721
AAC TCA TGG GCT CTG AGC AGT GGA GAA CAG TGG TGT GAA CGG GCA TCT CCT CCC
 N   S   W   A   L   S   S   G   E   Q   W   C   E   R   A   S   P   P 736                 751                 766
AGC AGC TCA TGC AAC ATC TCC TCT GGG GAA ATG CAG AAG GGC CTG TGG GAG CAG
 S   S   S   C   N   I   S   S   G   E   M   Q   K   G   L   W   E   Q 781                 796                 811                 826
TGC CAG CTT CTG AAG AGC ACC TCG GTG TTT GCC CGC TGC CAC CCT CTG GTG GAC
 C   Q   L   L   K   S   T   S   V   F   A   R   C   H   P   L   V   D 841                 856                 871                 886
CCC GAG CCT TTT GTG GCC CTG TGT GAG AAG ACT TTG TGT GAG TGT GCT GGG GGG
 P   E   P   F   V   A   L   C   E   K   T   L   C   E   C   A   G   G 901                 916                 931
CTG GAG TGC GCC TGC CCT GCC CTC CTG GAG TAC GCC CGG ACC TGT GCC CAG GAG
 L   E   C   A   C   P   A   L   L   E   Y   A   R   T   C   A   Q   E 946                 961                 976                 991
GGA ATG GTG CTG TAC GGC TGG ACC GAC CAC AGC GCG TGC AGC CCA GTG TGC CCT
 G   M   V   L   Y   G   W   T   D   H   S   A   C   S   P   V   C   P 1006                1021                1036
GCT GGT ATG GAG TAT AGG CAG TGT GTG TCC CCT TGC GCC AGG ACC TGC AGA GGC
 A   G   M   E   Y   R   Q   C   V   S   P   C   A   R   T   C   Q   S 1051                1066                1081                1096
CTG CAC ATC AAT GAA ATG TGT CAG GAG CGA TGC GTG GAT GGC TGC AGC TGC CCT
 L   H   I   N   E   M   C   Q   E   R   C   V   D   G   C   S   C   P 1111                1126                1141                1156
GAG GGA CAG CTC CTG GAT GAA GGC CTC TGC GTG GAG AGC ACC GAG TGT CCC TGC
 E   G   Q   L   L   D   E   G   L   C   V   E   S   T   E   C   P   C
```

TABLE 2-continued

LVWF cDNA sequence with deduced amino acid sequence

```
             1171                  1186                  1201
GTG CAT TCC GGA AAG CGC TAC CCT CCC GGC ACC TCC CTC TCT CGA GAC TGC AAC
 V   H   S   G   K   R   Y   P   P   G   T   S   L   S   R   D   C   N 1216                  1231                  1246                  1261
ACC TGC ATT TGC CGA AAC AGC CAG TGG ATC TGC AGC AAT GAA GAA TGT CCA GGG
 T   C   I   C   R   N   S   Q   W   I   C   S   N   E   E   C   P   G 1276                  1291                  1306
GAG TGC CTT GTC ACA GGT CAA TCA CAC TTC AAG AGC TTT GAC AAC AGA TAC TTC
 E   C   L   V   T   G   Q   S   H   F   K   S   F   D   N   R   Y   F 1321                  1336                  1351                  1366
ACC TTC AGT GGG ATC TGC CAG TAC CTG CTG GCC CGG GAT TGC CAG GAC CAC TCC
 T   F   S   G   I   C   Q   Y   L   L   A   R   D   C   Q   D   H   S 1381                  1396                  1411                  1426
TTC TCC ATT GTC ATT GAG ACT GTC CAG TGT GCT GAT GAC CGC GAC GCT GTG TGC
 F   S   I   V   I   E   T   V   Q   C   A   D   D   R   D   A   V   C 1441                  1456                  1471
ACC CGC TCC GTC ACC GTC CGG CTG CCT GGC CTG CAC AAC AGC CTT GTG AAA CTG
 T   R   S   V   T   V   R   L   P   G   L   H   N   S   L   V   K   L 1486                  1501                  1516                  1531
AAG CAT GGG GCA GGA GTT GCC ATG GAT GGC CAG GAC GTC CAG CTC CCC CTC CTG
 K   H   G   A   G   V   A   M   D   G   Q   D   V   Q   L   P   L   L 1546                  1561                  1576
AAA GGT GAC CTC CGC ATC CAG CAT ACA GTG ACG GCC TCC GTG CGC CTC AGC TAC
 K   G   D   L   R   I   Q   H   T   V   T   A   S   V   R   L   S   Y 1591                  1606                  1621                  1636
GGG GAG GAC CTG CAG ATG GAC TGG GAT GGC CGC GGG AGG CTG CTG GTG AAG CTG
 G   E   D   L   Q   M   D   W   D   G   R   G   R   L   L   V   K   L 1651                  1666                  1681                  1696
TCC CCC GTC TAT GCC GGG AAG ACC TGC GGC CTG TGT GGG AAT TAC AAT GGC AAC
 S   P   V   Y   A   G   K   T   C   G   L   C   G   N   Y   N   G   N 1711                  1726                  1741
CAG GGC GAC GAC TTC CTT ACC CCC TCT GGG CTG GCG GAG CCC CGG GTG GAG GAC
 Q   G   D   D   F   L   T   P   S   G   L   A   E   P   R   V   E   D 1756                  1771                  1786                  1801
TTC GGG AAC GCC TGG AAG CTG CAC GGG GAC TGC CAG GAC CTG CAG AAG CAG CAC
 F   G   N   A   W   K   L   H   G   D   C   Q   D   L   Q   K   Q   H 1816                  1831                  1846
AGC GAT CCC TGC GCC CTC AAC CCG CGC ATG ACC AGG TTC TCC GAG GAG GCG TGC
 S   D   P   C   A   L   N   P   R   M   T   R   F   S   E   E   A   C 1861                  1876                  1891                  1906
GCG GTC CTG ACG TCC CCC ACA TTC GAG GCC TGC CAT CGT GCC GTC AGC CCG CTG
 A   V   L   T   S   P   T   F   E   A   C   H   R   A   V   S   P   L 1921                  1936                  1951                  1966
CCC TAC CTG CGG AAC TGC CGC TAC GAC GTG TGC TCC TGC TCG GAC GGC CGC GAG
 P   Y   L   R   N   C   R   Y   D   V   C   S   C   S   D   G   R   E 1981                  1996                  2011
TGC CTG TGC GGC GCC CTG GCC AGC TAT GCC GCG GCC TGC GCG GGA AGA GGC GTG
 C   L   C   G   A   L   A   S   Y   A   A   A   C   A   G   R   G   V

2026
@           2041                  2056                  2071
CGC GTC GCG TGG CGC GAG CCA GGC CGC TGT GAG CTG AAC TGC CCG AAA GGC CAG
 R   V   A   W   R   E   P   G   R   C   E   L   N   C   P   K   G   Q 2086                  2101                  2116
GTG TAC CTG CAG TGC GGG ACC CCC TGC AAC CTG ACC TGC CGC TCT CTC TCT TAC
 V   Y   L   Q   C   G   T   P   C   N   L   T   C   R   S   L   S   Y 2131                  2146                  2161                  2176
CCG GAT GAG GAA TGT AAT GAG GCC TGC CTG GAG GGC TGC TTC TGC CCC CCA GGG
 P   D   E   E   C   N   E   A   C   L   E   G   C   F   C   P   P   G
```

TABLE 2-continued

LVWF cDNA sequence with deduced amino acid sequence

```
       2191            2206            2221            2236
CTC TAC ATG GAT GAG AGG GGG GAC TGC GTG CCC AAG GCC CAG TGC CCC TGT TAC
 L   Y   M   D   E   R   G   D   C   V   P   K   A   Q   C   P   C   Y 2251            2266            2281
TAT GAC GGT GAG ATC TTC CAG CCA GAA GAC ATC TTC TCA GAC CAT CAC ACC ATG
 Y   D   G   E   I   F   Q   P   E   D   I   F   S   D   H   H   T   M 2296            2311            2326            2341
TGC TAC TGT GAG GAT GGC TTC ATG CAC TGT ACC ATG AGT GGA GTC CCC GGA AGC
 C   Y   C   E   D   G   F   M   H   C   T   M   S   G   V   P   G   S 2356            2371            2386
TTG CTG CCT GAC GCT GTC CTC AGC AGT CCC CTG TCT CAT CGC AGC AAA AGG AGC
 L   L   P   D   A   V   L   S   S   P   L   S   H   R   S   K   R   S 2401            2416            2431            2446
CTA TCC TGT CGG CCC CCC ATG GTC AAG CTG GTG TGT CCC GCT GAC AAC CTG CGG
 L   S   C   R   P   P   M   V   K   L   V   C   P   A   D   N   L   R 2461            2476            2491            2506
GCT GAA GGG CTC GAG TGT ACC AAA ACG TGC CAG AAC TAT GAC CTG GAG TGC ATG
 A   E   G   L   E   C   T   K   T   C   Q   N   Y   D   L   E   C   M 2521            2536            2551
AGC ATG GGC TGT GTC TCT GGC TGC CTC TGC CCC CCG GGC ATG GTC CGG CAT GAG
 S   M   G   C   V   S   G   C   L   C   P   P   G   M   V   R   H   E 2566            2581            2596            2611
AAC AGA TGT GTG GCC CTG GAA AGG TGT CCC TGC TTC CAT CAG GGC AAG GAG TAT
 N   R   C   V   A   L   E   R   C   P   C   F   H   Q   G   K   E   Y 2626            2641            2656
GCC CCT GGA GAA ACA GTG AAG ATT GGC TGC AAC ACT TGT GTC TGT CGG GAC CGG
 A   P   G   E   T   V   K   I   G   C   N   T   C   V   C   R   D   R 2671            2686            2701            2716
AAG TGG AAC TGC ACA GAC CAT GTG TGT GAT GCC ACG TGC TCC ACG ATC GGC ATG
 K   W   N   C   T   D   H   V   C   D   A   T   C   S   T   I   G   M 2731            2746            2761            2776
GCC CAC TAC CTC ACC TTC GAC GGG CTC AAA TAC CTG TTC CCC GGG GAG TGC CAG
 A   H   Y   L   T   F   D   G   L   K   Y   L   F   P   G   E   C   Q 2791            2806            2821
TAC GTT CTG GTG CAG GAT TAC TGC GGC AGT AAC CCT GGG ACC TTT CGG ATC CTA
 Y   V   L   V   Q   D   Y   C   G   S   N   P   G   T   F   R   I   L 2836            2851            2866            2881
GTG GGG AAT AAG GGA TGC AGC CAC CCC TCA GTG AAA TGC AAG AAA CGG GTC ACC
 V   G   N   K   G   C   S   H   P   S   V   K   C   K   K   R   V   T 2896            2911            2926
ATC CTG GTG GAG GGA GGA GAG ATT GAG CTG TTT GAC GGG GAG GTG AAT GTG AAG
 I   L   V   E   G   G   E   I   E   L   F   D   G   E   V   N   V   K 2941            2956            2971            2986
AGG CCC ATG AAG GAT GAG ACT CAC TTT GAG GTG GTG GAG TCT GGC CGG TAC ATC
 R   P   M   K   D   E   T   H   F   E   V   V   E   S   G   R   Y   I 3001            3016            3031            3046
ATT CTG CTG CTG GGC AAA GCC CTC TCC GTG GTC TGG GAC CGC CAC CTG AGC ATC
 I   L   L   L   G   K   A   L   S   V   V   W   D   R   H   L   S   I 3061            3076            3091
TCC GTG GTC CTG AAG CAG ACA TAC CAG GAG AAA GTG TGT GGC CTG TGT GGG AAT
 S   V   V   L   K   Q   T   Y   Q   E   K   V   C   G   L   C   G   N 3106            3121            3136            3151
TTT GAT GGC ATC CAG AAC AAT GAC CTC ACC AGC AGC AAC CTC CAA GTG GAG GAA
 F   D   G   I   Q   N   N   D   L   T   S   S   N   L   Q   V   E   E 3166            3181            3196
GAC CCT GTG GAC TTT GGG AAC TCC TGG AAA GTG AGC TCG CAG TGT GCT GAC ACC
 D   P   V   D   F   G   N   S   W   K   V   S   S   Q   C   A   D   T
```

TABLE 2-continued

LVWF cDNA sequence with deduced amino acid sequence

```
      3211            3226                3241                3256
AGA AAA GTG CCT CTG GAC TCA TCC CCT GCC ACC TGC CAT AAC AAC ATC ATG AAG
 R   K   V   P   L   D   S   S   P   A   T   C   H   N   N   I   M   K 3271                3286                3301                3316
CAG ACG ATG GTG GAT TCC TCC TGT AGA ATC CTT ACC AGT GAC GTC TTC CAG GAC
 Q   T   M   V   D   S   S   C   R   I   L   T   S   D   V   F   Q   D 3331                3346                3361
TGC AAC AAG CTG GTG GAC CCC GAG CCA TAT CTG GAT GTC TGC ATT TAC GAC ACC
 C   N   K   L   V   D   P   E   P   Y   L   D   V   C   I   Y   D   T 3376                3391                3406                3421
TGC TCC TGT GAG TCC ATT GGG GAC TGC GCC TGC TTC TGC GAC ACC ATT GCT GCC
 C   S   C   E   S   I   G   D   C   A   C   F   C   D   T   I   A   A 3436                3451                3466
TAT GCC CAC GTG TGT GCC CAG CAT GGC AAG GTG GTG ACC TGG AGG ACG GCC ACA
 Y   A   H   V   C   A   Q   H   G   K   V   V   T   W   R   T   A   T 3481            3496                3511                3526
TTG TGC CCC CAG AGC TGC GAG GAG AGG AAT CTC CGG GAG AAC GGG TAT GAG TGT
 L   C   P   Q   S   C   E   E   R   N   L   R   E   N   G   Y   E   C 3541                3556                3571                3586
GAG TGG CGC TAT AAC AGC TGT GCA CCT GCC TGT CAA GTC ACG TGT CAG CAC CCT
 E   W   R   Y   N   S   C   A   P   A   C   Q   V   T   C   Q   H   P 3601                3616                3631
GAG CCA CTG GCC TGC CCT GTG CAG TGT GTG GAG GGC TGC CAT GCC CAC TGC CCT
 E   P   L   A   C   P   V   Q   C   V   E   G   C   H   A   H   C   P 3646                3661                3676                3691
CCA GGG AAA ATC CTG GAT GAG CTT TTG CAG ACC TGC GTT GAC CCT GAA GAC TGT
 P   G   K   I   L   D   E   L   L   Q   T   C   V   D   P   E   D   C 3706                3721                3736
CCA GTG TGT GAG GTG GCT GGC CGG CGT TTT GCC TCA GGA AAG AAA GTC ACC TTG
 P   V   C   E   V   A   G   R   R   F   A   S   G   K   K   V   T   L 3751            3766                3781                3796
AAT CCC AGT GAC CCT GAG CAC TGC CAG ATT TGC CAC TGT GAT GTT GTC AAC CTC
 N   P   S   D   P   E   H   C   Q   I   C   H   C   D   V   V   N   L 3811                3826                3841                3856
ACC TGT GAA GCC TGC CAG GAG CCG GGA GGC CTG GTG GTG CCT CCC ACA GAT GCC
 T   C   E   A   C   Q   E   P   G   G   L   V   V   P   P   T   D   A 3871                3886                3901
CCG GTG AGC CCC ACC ACT CTG TAT GTG GAG GAC ATC TCG GAA CCG CCG TTG CAC
 P   V   S   P   T   T   L   Y   V   E   D   I   S   E   P   P   L   H 3916                3931                3946                3961
GAT TTC TAC TGC AGC AGG CTA CTG GAC CTG GTC TTC CTG CTG GAT GGC TCC TCC
 D   F   Y   C   S   R   L   L   D   L   V   F   L   L   D   G   S   S 3976                3991                4006
AGG CTG TCC GAG GCT GAG TTT GAA GTG CTG AAG GCC TTT GTG GTG GAC ATG ATG
 R   L   S   E   A   E   F   E   V   L   K   A   F   V   V   D   M   M 4021            4036                4051                4066
GAG CGG CTG CGC ATC TCC CAG AAG TGG GTC CGC GTG GCC GTG GTG GAG TAC CAC
 E   R   L   R   I   S   Q   K   W   V   R   V   A   V   V   E   Y   H 4081                4096                4111                4126
GAC GGC TCC CAC GCC TAC ATC GGG CTC AAG GAC CGG AAG CGA CCG TCA GAG CTG
 D   G   S   H   A   Y   I   G   L   K   D   R   K   R   P   S   E   L 4141                4156                4171
CGG CGC ATT GCC AGC CAG GTG AAG TAT GCG GGC AGC CAG GTG GCC TCC ACC AGC
 R   R   I   A   S   Q   V   K   Y   A   G   S   Q   V   A   S   T   S 4186                4201                4216                4231
GAG GTC TTG AAA TAC ACA CTG TTC CAA ATC TTC AGC AAG ATC GAC CGC CCT GAA
 E   V   L   K   Y   T   L   F   Q   I   F   S   K   I   D   R   P   E
```

TABLE 2-continued

LVWF cDNA sequence with deduced amino acid sequence

```
            4246              4261              4276
GCC TCC CGC ATC GCC CTG CTC CTG ATG GCC AGC CAG GAG CCC CAA CGG ATG TCC
 A   S   R   I   A   L   L   L   M   A   S   Q   E   P   Q   R   M   S 4291              4306              4321              4336
CGG AAC TTT GTC CGC TAC GTC CAG GGC CTG AAG AAG AAG AAG GTC ATT GTG ATC
 R   N   F   V   R   Y   V   Q   G   L   K   K   K   K   V   I   V   I 4351              4366              4381              4396
CCG GTG GGC ATT GGG CCC CAT GCC AAC CTC AAG CAG ATC CGC CTC ATC GAG AAG
 P   V   G   I   G   P   H   A   N   L   K   Q   I   R   L   I   E   K 4411              4426              4441
CAG GCC CCT GAG AAC AAG GCC TTC GTG CTG AGC AGT GTG GAT GAG CTG GAG CAG
 Q   A   P   E   N   K   A   F   V   L   S   S   V   D   E   L   E   Q 4456              4471              4486              4501
CAA AGG GAC GAG ATC GTT AGC TAC CTC TGT GAC CTT GCC CCT GAA GCC CCT CCT
 Q   R   D   E   I   V   S   Y   L   C   D   L   A   P   E   A   P   P 4516              4531              4546
CCT ACT CTG CCC CCC CAC ATG GCA CAA GTC ACT GTG GGC CCG GGG CTC TTG GGG
 P   T   L   P   P   H   M   A   Q   V   T   V   G   P   G   L   L   G 4561              4576              4591              4606
GTT TCG ACC CTG GGG CCC AAG AGG AAC TCC ATG GTT CTG GAT GTG GCG TTC GTC
 V   S   T   L   G   P   K   R   N   S   M   V   L   D   V   A   F   V 4621              4636              4651              4666
CTG GAA GGA TCG GAC AAA ATT GGT GAA GCC GAC TTC AAC AGG AGC AAG GAG TTC
 L   E   G   S   D   K   I   G   E   A   D   F   N   R   S   K   E   F 4681              4696              4711
ATG GAG GAG GTG ATT CAG CGG ATG GAT GTG GGC CAG GAC AGC ATC CAC GTC ACG
 M   E   E   V   I   Q   R   M   D   V   G   Q   D   S   I   H   V   T 4726              4741              4756              4771
GTG CTG CAG TAC TCC TAC ATG GTG ACC GTG GAG TAC CCC TTC AGC GAG GCA CAG
 V   L   Q   Y   S   Y   M   V   T   V   E   Y   P   F   S   E   A   Q 4786              4801              4816
TCC AAA GGG GAC ATC CTG CAG CGG GTG CGA GAG ATC GCC TAC CAG GGC GGC AAC
 S   K   G   D   I   L   Q   R   V   R   E   I   A   Y   Q   G   G   N 4831              4846              4861              4876
AGG ACC AAC ACT GGG CTG GCC CTG CGG TAC CTC TCT GAC CAC AGC TTC TTG GTC
 R   T   N   T   G   L   A   L   R   Y   L   S   D   H   S   F   L   V 4891              4906              4921              4936
AGC CAG GGT GAC CGG GAG CAG GCG CCC AAC CTG GTC TAC ATG GTC ACC GGA AAT
 S   Q   G   D   R   E   Q   A   P   N   L   V   Y   M   V   T   G   N 4951              4966              4981
CCT GCC TCT GAT GAG ATC AAG AGG CTG CCT GGA GAC ATC CAG GTG GTG CCC ATT
 P   A   S   D   E   I   K   R   L   P   G   D   I   Q   V   V   P   I 4996              5011              5026              5041
GGA GTG GGC CCT AAT GCC AAC GTG CAG GAG CTG GAG AGG ATT GGC TGG CCC AAT
 G   V   G   P   N   A   N   V   Q   E   L   E   R   I   G   W   P   N 5056              5071              5086
GCC CCT ATC CTC ATC CAG GAC TTT GAG ACG CTC CCC CGA GAG GCT CCT GAC CTG
 A   P   I   L   I   Q   D   F   E   T   L   P   R   E   A   P   D   L 5101              5116              5131              5146
GTG CTG CAG AGG TGC TGC TCC GGA GAG GGG CTG CAG ATC CCC ACC CTC TCC CCT
 V   L   Q   R   C   C   S   G   E   G   L   Q   I   P   T   L   S   P 5161              5176              5191              5206
GCA CCT GAC TGC AGC CAG CCC CTG GAC GTG ATC CTT CTC CTG GAT GGC TCC TCC
 A   P   D   C   S   Q   P   L   D   V   I   L   L   L   D   G   S   S 5221              5236              5251
AGT TTC CCA GCT TCT TAT TTT GAT GAA ATG AAG AGT TTC GCC AAG GCT TTC ATT
 S   F   P   A   S   Y   F   D   E   M   K   S   F   A   K   A   F   I
```

TABLE 2-continued

LVWF cDNA sequence with deduced amino acid sequence

```
           5266              5281              5296              5311
   TCA AAA GCC AAT ATA GGG CCT CGT CTC ACT CAG GTG TCA GTG CTG CAG TAT GGA
    S   K   A   N   I   G   P   R   L   T   Q   V   S   V   L   Q   Y   G 5326              5341              5356
   AGC ATC ACC ACC ATT GAC GTG CCA TGG AAC GTG GTC CCG GAG AAA GCC CAT TTG
    S   I   T   T   I   D   V   P   W   N   V   V   P   E   K   A   H   L 5371                5386              5401              5416
   CTG AGC CTT GTG GAC GTC ATG CAG CGG GAG GGA GGC CCC AGC CAA ATC GGG GAT
    L   S   L   V   D   V   M   Q   R   E   G   G   P   S   Q   I   G   D 5431              5446              5461              5476
   GCC TTG GGC TTT GCT GTG CGA TAC TTG ACT TCA GAA ATG CAT GGT GCC AGG CCG
    A   L   G   F   A   V   R   Y   L   T   S   E   M   H   G   A   R   P 5491              5506              5521
   GGA GCC TCA AAG GCG GTG GTC ATC CTG GTC ACG GAC GTC TCT GTG GAT TCA GTG
    G   A   S   K   A   V   V   I   L   V   T   D   V   S   V   D   S   V 5536              5551              5566              5581
   GAT GCA GCA GCT GAT GCC GCC AGG TCC AAC AGA GTG ACA GTG TTC CCT ATT GGA
    D   A   A   A   D   A   A   R   S   N   R   V   T   V   F   P   I   G 5596              5611              5626
   ATT GGA GAT CGC TAC GAT GCA GCC CAG CTA CGG ATC TTG GCA GGC CCA GCA GGC
    I   G   D   R   Y   D   A   A   Q   L   R   I   L   A   G   P   A   G 5641                5656              5671              5686
   GAC TCC AAC GTG GTG AAG CTC CAG CGA ATC GAA GAC CTC CCT ACC ATG GTC ACC
    D   S   N   V   V   K   L   Q   R   I   E   D   L   P   T   M   V   T 5701              5716              5731              5746
   TTG GGC AAT TCC TTC CTC CAC AAA CTG TGC TCT GGA TTT GTT AGG ATT TGC ATG
    L   G   N   S   F   L   H   K   L   C   S   G   F   V   R   I   C   M 5761              5776              5791
   GAT GAG GAT GGG AAT GAG AAG AGG CCC GGG GAC GTC TGG ACC TTG CCA GAC CAG
    D   E   D   G   N   E   K   R   P   G   D   V   W   T   L   P   D   Q 5806              5821              5836              5851
   TGC CAC ACC GTG ACT TGC CAG CCA GAT GGC CAG ACC TTG CTG AAG AGT CAT CGG
    C   H   T   V   T   C   Q   P   D   G   Q   T   L   L   K   S   H   R 5866              5881              5896
   GTC AAC TGT GAC CGG GGG CTG AGG CCT TCG TGC CCT AAC AGC AGG TCC CCT GTT
    V   N   C   D   R   G   L   R   P   S   C   P   N   S   Q   S   P   V 5911                5926              5941              5956
   AAA GTG GAA GAG ACC TGT GGC TGC CGC TGG ACC TGC CCC TGC GTG TGC ACA GGC
    K   V   E   E   T   C   G   C   R   W   T   C   P   C   V   C   T   G 5971              5986              6001              6016
   AGC TCC ACT CGG CAC ATC GTG ACC TTT GAT GGG CAG AAT TTC AAG CTG ACT GGC
    S   S   T   R   H   I   V   T   F   D   G   Q   N   F   K   L   T   G 6031              6046              6061
   AGC TGT TCT TAT GTC CTA TTT CAA AAC AAG GAG CAG GAC CTG GAG GTG ATT CTC
    S   C   S   Y   V   L   F   Q   N   K   E   Q   D   L   E   V   I   L 6076              6091              6106              6121
   CAT AAT GGT GCC TGC AGC CCT GGA GCA AGG CAG GGC TGC ATG AAA TCC ATC GAG
    H   N   G   A   C   S   P   G   A   R   Q   G   C   M   K   S   I   E 6136              6151              6166
   GTG AAG CAC AGT GCC CTC TCC GTC GAG CTG CAC AGT GAC ATG GAG GTG ACG GTG
    V   K   H   S   A   L   S   V   E   L   H   S   D   M   E   V   T   V 6181                6196              6211              6226
   AAT GGG AGA CTG GTC TCT GTT CCT TAC GTG GGT GGG AAC ATG GAA GTC AAC GTT
    N   G   R   L   V   S   V   P   Y   V   G   G   N   M   E   V   N   V 6241              6256              6271              6286
   TAT GGT GCC ATC ATG CAT GAG GTC AGA TTC AAT CAC CTT GGT CAC ATC TTC ACA
    Y   G   A   I   M   H   E   V   R   F   N   H   L   G   H   I   F   T
```

TABLE 2-continued

LVWF cDNA sequence with deduced amino acid sequence

```
            6301                  6316                  6331
TTC ACT CCA CAA AAC AAT GAG TTC CAA CTG CAG CTC AGC CCC AAG ACT TTT GCT
 F   T   P   Q   N   N   E   F   Q   L   Q   L   S   P   K   T   F   A 6346                  6361                  6376                  6391
TCA AAG ACG TAT GGT CTG TGT GGG ATC TGT GAT GAG AAC GGA GCC AAT GAC TTC
 S   K   T   Y   G   L   C   G   I   C   D   E   N   G   A   N   D   F 6406                  6421                  6436
ATG CTG AGG GAT GGC ACA GTC ACC ACA GAC TGG AAA ACA CTT GTT CAG GAA TGG
 M   L   R   D   G   T   V   T   T   D   W   K   T   L   V   Q   E   W 6451                  6466                  6481                  6496
ACT GTG CAG CGG CCA GGG CAG ACG TGC CAG CCC ATC CTG GAG GAG CAG TGT CTT
 T   V   Q   R   P   G   Q   T   C   Q   P   I   L   E   E   Q   C   L 6511                  6526                  6541                  6556
GTC CCC GAC AGC TCC CAC TGC CAG GTC CTC CTC TTA CCA CTG TTT GCT GAA TGC
 V   P   D   S   S   H   C   Q   V   L   L   L   P   L   F   A   E   C 6571                  6586                  6601
CAC AAG GTC CTG GCT CCA GCC ACA TTC TAT GCC ATC TGC CAG CAG GAC AGT TGC
 H   K   V   L   A   P   A   T   F   Y   A   I   C   Q   Q   D   S   C 6616                  6631                  6646                  6661
CAC CAG GAG CAA GTG TGT GAG GTG ATC GCC TCT TAT GCC CAC CTC TGT CGG ACC
 H   Q   E   Q   V   C   E   V   I   A   S   Y   A   H   L   C   R   T 6676                  6691                  6706
AAC GGG GTC TGC GTT GAC TGG AGG ACA CCT GAT TTC TGT GCT ATG TCA TGC CCA
 N   G   V   C   V   D   W   R   T   P   D   F   C   A   M   S   C   P 6721                  6736                  6751                  6766
CCA TCT CTG GTC TAC AAC CAC TGT GAG CAT GGC TGT CCC CGG CAC TGT GAT GGC
 P   S   L   V   Y   N   H   C   E   H   G   C   P   R   H   C   D   G 6781                  6796                  6811                  6826
AAC GTG AGC TCC TGT GGG GAC CAT CCC TCC GAA GGC TGT TTC TGC CCT CCA GAT
 N   V   S   S   C   G   D   H   P   S   E   G   C   F   C   P   P   D 6841                  6856                  6871
AAA GTC ATG TTG GAA GGC AGC TGT GTC CCT GAA GAG GCC TGC ACT CAG TGC ATT
 K   V   M   L   E   G   S   C   V   P   E   E   A   C   T   Q   C   I 6886                  6901                  6916                  6931
GGT GAG GAT GGA GTC CAG CAC CAG TTC CTG GAA GCC TGG GTC CCG GAC CAC CAG
 G   E   D   G   V   Q   H   Q   F   L   E   A   W   V   P   D   H   Q 6946                  6961                  6976
CCC TGT CAG ATC TGC ACA TGC CTC AGC GGG CGG AAG GTC AAC TGC ACA ACG CAG
 P   C   Q   I   C   T   C   L   S   G   R   K   V   N   C   T   T   Q 6991                  7006                  7021                  7036
CCC TGC CCC ACG GCC AAA GCT CCC ACG TGT GGC CTG TGT GAA GTA GCC CGC CTC
 P   C   P   T   A   K   A   P   T   C   G   L   C   E   V   A   R   L 7051                  7066                  7081                  7096
CGC CAG AAT GCA GAC CAG TGC TGC CCC GAG TAT GAG TGT GTG TGT GAC CCA GTG
 R   Q   N   A   D   Q   C   C   P   E   Y   E   C   V   C   D   P   V 7111                  7126                  7141
AGC TGT GAC CTG CCC CCA GTG CCT CAC TGT GAA CGT GGC CTC CAG CCC ACA CTG
 S   C   D   L   P   P   V   P   H   C   E   R   G   L   Q   P   T   L 7156                  7171                  7186                  7201
ACC AAC CCT GGC GAG TGC AGA CCC AAC TTC ACC TGC GCC TGC AGG AAG GAG GAG
 T   N   P   G   E   C   R   P   N   F   T   C   A   C   R   K   E   E 7216                  7231                  7246
TGC AAA AGA GTG TCC CCA CCC TCC TGC CCC CCG CAC CGT TTG CCC ACC CTT CGG
 C   K   R   V   S   P   P   S   C   P   P   H   R   L   P   T   L   R 7261                  7276                  7291                  7306
AAG ACC CAG TGC TGT GAT GAG TAT GAG TGT GCC TGC AAC TGT GTC AAC TCC ACA
 K   T   Q   C   C   D   E   Y   E   C   A   C   N   C   V   N   S   T
```

TABLE 2-continued

LVWF cDNA sequence with deduced amino acid sequence

```
            7321              7336              7351                 7366
     GTG AGC TGT CCC CTT GGG TAC TTG GCC TCA ACC GCC ACC AAT GAC TGT GGC TGT
      V   S   C   P   L   G   Y   L   A   S   T   A   T   N   D   C   G   C 7381              7396              7411
     ACC ACA ACC ACC TGC CTT CCC GAC AAG GTG TGT GTC CAC CGA AGC ACC ATC TAC
      T   T   T   T   C   L   P   D   K   V   C   V   H   R   S   T   I   Y 7426              7441              7456                 7471
     CCT GTG GGC CAG TTC TGG GAG GAG GGC TGC GAT GTG TGC ACC TGC ACC GAC ATG
      P   V   G   Q   F   W   E   E   G   C   D   V   C   T   C   T   D   M 7486              7501              7516
     GAG GAT GCC GTG ATG GGC CTC CGC GTG GCC CAG TGC TCC CAG AAG CCC TGT GAG
      E   D   A   V   M   G   L   R   V   A   Q   C   S   Q   K   P   C   E 7531              7546              7561              7576
     GAC AGC TGT CGG TCG GGC TTC ACT TAC GTT CTG CAT GAA GGC GAG TGC TGT GGA
      D   S   C   R   S   G   F   T   Y   V   L   H   E   G   E   C   C   G 7591              7606              7621              7636
     AGG TGC CTG CCA TCT GCC TGT GAG GTG GTG ACT GGC TCA CCG CGG GGG GAC TCC
      R   C   L   P   S   A   C   E   V   V   T   G   S   P   R   G   D   S 7651              7666              7681
     CAG TCT TCC TGG AAG AGT GTC GGC TCC CAG TGG GCC TCC CCG GAG AAC CCC TGC
      Q   S   S   W   K   S   V   G   S   Q   W   A   S   P   E   N   P   C 7696              7711              7726                 7741
     CTC ATC AAT GAG TGT GTC CGA GTG AAG GAG GAG GTC TTT ATA CAA CAA AGG AAC
      L   I   N   E   C   V   R   V   K   E   E   V   F   I   Q   Q   R   N 7756              7771              7786
     GTC TCC TGC CCC CAG CTG GAG GTC CCT GTC TGC CCC TCG GGC TTT CAG CTG AGC
      V   S   C   P   Q   L   E   V   P   V   C   P   S   G   F   Q   L   S 7801              7816              7831              7843
     TGT AAG ACC TCA GCG TGC TGC CCA AGC TGT CGC TGT GAG CGC ATG GAG GCC TGC
      C   K   T   S   A   C   C   P   S   C   R   C   E   R   M   E   A   C 7861              7876              7891              7906
     ATG CTC AAT GGC ACT GTC ATT GGG CCC GGG AAG ACT GTG ATG ATC GAT GTG TGC
      M   L   N   G   T   V   I   G   P   G   K   T   V   M   I   D   V   C 7921              7936              7951
     ACG ACC TGC CGC TGC ATG GTG CAG GTG GGG GTC ATC TCT GGA TTC AAG CTG GAG
      T   T   C   R   C   M   V   Q   V   G   V   I   S   G   F   K   L   E 7966              7981              7996                 8011
     TGC AGG AAG ACC ACC TGC AAC CCC TGC CCC CTG GGT TAC AAG GAA GAA AAT AAC
      C   R   K   T   T   C   N   P   C   P   L   G   Y   K   E   E   N   N 8026              8041              8056
     ACA GGT GAA TGT TGT GGG AGA TGT TTG CCT ACG GCT TGC ACC ATT CAG CTA AGA
      T   G   E   C   C   G   R   C   L   P   T   A   C   T   I   Q   L   R 8071              8086              8101              8116
     GGA GGA CAG ATC ATG ACA CTG AAG CGT GAT GAG ACG CTC CAG GAT GGC TGT GAT
      G   G   Q   I   M   T   L   K   R   D   E   T   L   Q   D   G   C   D 8131              8146              8161              8176
     ACT CAC TTC TGC AAG GTC AAT GAG AGA GGA GAG TAC TTC TGG GAG AAG AGG GTC
      T   H   F   C   K   V   N   E   R   G   E   Y   F   W   E   K   R   V 8191              8206              8221
     ACA GGC TGC CCA CCC TTT GAT GAA CAC AAG TGT CTG GCT GAG GGA GGT AAA ATT
      T   G   C   P   P   F   D   E   H   K   C   L   A   E   G   G   K   I 8236              8251              8266                 8281
     ATG AAA ATT CCA GGC ACC TGC TGT GAC ACA TGT GAG GAG CCT GAG TGC AAC GAC
      M   K   I   P   G   T   C   C   D   T   C   E   E   P   E   C   N   D 8296              8311              8326
     ATC ACT GCC AGG CTG CAG TAT GTC AAG GTG GGA AGC TGT AAG TCT GAA GTA GAG
      I   T   A   R   L   Q   Y   V   K   V   G   S   C   K   S   E   V   E
```

TABLE 2-continued

LVWF cDNA sequence with deduced amino acid sequence

```
8341              8356              8371              8386
GTG GAT ATC CAC TAC TGC CAG GGC AAA TGT GCC AGC AAA GCC ATG TAC TCC ATT
 V   D   I   H   Y   C   Q   G   K   C   A   S   K   A   M   Y   S   I 8401              8416              8431              8446
GAC ATC AAC GAT GTG CAG GAC CAG TGC TCC TGC TGC TCT CCG ACA CGG ACG GAG
 D   I   N   D   V   Q   D   Q   C   S   C   C   S   P   T   R   T   E 8461              8476              8491
CCC ATG CAG GTG GCC CTG CAC TGC ACC AAT GGC TCT GTT GTG TAC CAT GAG GTT
 P   M   Q   V   A   L   H   C   T   N   G   S   V   V   Y   H   E   V 8506              8521              8536                      8558
CTC AAT GCC ATG GAG TGC AAA TGC TCC CCC AGG AAG TGC AGC AAG TGA GGCTGCTGCA
 L   N   A   M   E   C   K   C   S   P   R   K   C   S   K   .

8568       8578       8588
GCTGCATGGG TGCCTGCTGC TGCCGGAATT
```

300 kd., even before the extra contribution from glycosylation is taken into account. SDS-polyacrylamide gels are known to be an inaccurate way to estimate molecular weights in this range, although it has not been formally excluded that multi-step processing occurs, with rapid formation of a relatively stable 260 kd intermediate. Since the VWF "pro-piece" can be found intact in the circulation as a 100 kd glycoprotein, multi-stage processing seems unlikely and the pro-VWF is clearly larger than previously suspected and processed in a single step.

The function, if any, of the large VWF pro-piece, is currently unknown. Its fate after trans-membrane secretion is also not fully clear. However, the identity of the VWF propiece with a 10 Kd plasma glycoprotein has recently been established so that at least some of the intact pro-piece leaves the cell. The N-terminal sequence of the 100 Kd glycoprotein which corresponds to the predicted sequence of the propolypeptide implies that signal peptide cleavage occurs at the position shown by the arrow in Table 2. This agrees with the consensus sequences usually involved in signal peptidase cleavage (Watson, Nucl. Acids Res., 12: 5145-5164 (1984)).

Sadler et al., Proc. Natl. Acad. Sci. USA 82: 6394-6398 (1985) have recently published a partial VWF sequence, and noted the presence of repeated elements. Analysis of the complete nucleotide sequence, however, reveals much more extensive repetition in the VWF structure than shown by previous data. We confirm the presence of three complete copies of a repeat labelled "domain A" by Sadler et al. We have retained the terminology for this repeat and have confirmed the homology of the 5' end of its first copy, missing in the clones of Sadler et al. A striking feature, not noted by those authors, is the paucity of cys residues within this region, which occupies about 600 amino-acids in the center of the VWF sequence. In contrast, the regions at each end of the molecule, from nucleotides 208 to 3833, and 5729 to 8582 in our sequence, are extremely rich in Cys, and account almost entirely for the high Cys content of VWF. Cys is in fact the most abundant amino-acid in the prepro-VWF sequence, accounting for 8.3% of the residues. In the region outside "domain A", Cys accounts for 10.4% of the amino acids.

Further analysis of these Cys rich regions indicates that they too can be arranged as a series of 6 repeats of a basic 400 amino acid unit. The first repeat block begins almost immediately after the signal peptide. The second repeat is truncated just preceding this duplication and contains the cleavage site between the pro-piece and mature VWF. Following the third repeat, the sequence is interrupted by the triplicated cys-poor "A domain" repeat, after which the Cys rich repeats resume encoding the C-terminal end of the molecule. The fifth and sixth repeats are incomplete, but include the region of the short "B domain" repeats of Sadler et al. Those authors' "C domain" repeats follow in two copies. Since no free sulfhydryl groups can be detected in multimeric VWF, all these Cys residues are involved in interchain and intrachain disulfide bonds which are important determinants of the tertiary and quaternary structure of the protein.

B. Analyzing Sample DNA

DNA sequence polymorphisms are neutral variations in DNA sequence present throughout the genome, which can often be detected by restriction enzyme digestion and blot hybridization analysis. By neutral we mean that the variations per se are not themselves responsible for any phenotypic trait. However, the value of polymorphisms is that they are linked to or associated with adjacent portions of the genome, and therefore they can be used as markers of those portions of the genome.

Two types of DNA sequence polymorphisms have been described. One type involves single nucleotide changes, or small insertions or deletions, which result in the presence or absence of a particular restriction enzyme recognition site. In another type of polymorphism, a large segment of DNA of unknown function varies widely in length among individuals. Both types of sequence differences are inherited in Mendelian fashion.

RFLP's linked to the VWF gene are identified in genomic DNA from individuals examined by cutting sample DNA with a series of restriction enzymes. The resulting restriction length fragments are segregated by molecular weight. Hybridization with a radiolabeled VWF cDNA probe, e.g., the cDNA insert from clone pVWE6 yields (e.g., using Southern blot techniques) a unique band pattern. For example, RFLP's are detected by the above procedure using restriction enzymes TaqI and SacI and the pVWE6 probe. Specifically, peripheral blood specimens are collected in 10% acid-citrate-dextrose. High molecular weight DNA is prepared by standard techniques either from dextran sedimented leukocytes or isolated nuclei separated by centrifugation following TRITON X-100TH (t-octylphenoxypolyethoxyethanol) solubilization. From 2 to 16 g of DNA are digested to completion with the restriction enzymes TaqI and SacI. DNA fragments are then fractioned by electrophoresis in 0.6 to 1.0% agarose gels and transferred to nitrocellulose filters. The probes constructed from pVWE6 are labeled and hybridized with the DNA on the above-described nitrocellulose filters. The hybridized filters are washed and examined by autoradiography. Once identified RFLP's can be used as described above to assay a sample of human DNA and determine the source of a VWF gene in that sample. For example, DNA of parents and other family members can be screened, e.g., by Southern blotting, with such a probe, and then fetal DNA can be screened to determine the inheritance pattern of its VWF alleles.

Other Embodiments

Other embodiments are within the following claims. For example, the techniques described apply to other mammalian systems. Other RFLP's can be used. Hybridization probes can be used for other assays or research techniques.

What is claimed is:

1. A recombinant method of producing a functional human von Willebrand Factor protein that can be recognized by anti-von Willebrand Factor antibodies, wherein the method comprises the steps of
    (1) culturing a host cell from a mammalian cell line, wherein the host cell is transformed with an expression vector which comprises
        (a) the von Willebrand Factor-encoding nucleotide sequences of
            (i) pVWH33 (ATCC No. 53090),
            (ii) pVWH5 (ATCC No. 53088), and
            (iii) the sequence of nucleotides 9 through 587 of Table 1,
            wherein the sequences are combined 5'3' in the order (i), (ii), and (iii), and
        (b) heterologous DNA effective to cause expression of the von Willebrand Factor-encoding nucleotide sequences, wherein the culturing is performed in a culture medium and under conditions permitting the transformed host cell to express functional von Willebrand Factor protein that can be recognized by anti-von Willebrand Factor antibodies, and
    (2) recovering the functional von Willebrand Factor protein from step 1.

2. A method according to claim 1, wherein the combined von Willebrand Factor-encoding nucleotide sequences have a combined nucleotide sequence that is set forth in Table 2.

3. A recombinant method of producing functional human von Willebrand Factor proteins that can be recognized by anti-von Willebrand Factor antibodies, wherein the method comprises
    (1) culturing in media transformed host cells from a mammalian cell line, wherein such a transformed host cell comprises an expression vector that comprises a DNA sequence that comprises an open reading frame that is 8 to 9 kb in length and encodes functional human von Willebrand Factor protein having an amino acid sequence that is set forth in Table 2, and wherein the culturing allows the transformed host cell to produce the functional human von Willebrand Factor protein, and
    (2) obtaining functional human von Willebrand Factor proteins produced by the mammalian host cells of step 1.

4. The method according to claim 3, wherein the transformed host cells are selected from the group consisting of COS cells and CHO cells.

5. The method according to claim 3, wherein the open reading frame comprises 8439 nucleotides.

6. The method according to claim 4, wherein the host cells are CHO cells.

7. A recombinant product useful for treating a bleeding disorder, wherein the recombinant product comprises functional human von Willebrand Factor proteins that can be recognized by anti-von Willebrand Factor antibodies and are recombinantly expressed in transformed host cells from a mammalian cell line, wherein such a transformed host cell comprises an expression vector comprising DNA comprising the von Willebrand-encoding nucleotide sequences of
    (i) pVWH33 (ATCC No. 53090),
    (ii) pVWH5 (ATCC No. 53088), and
    (iii) the sequence of nucleotides 9 through 587 of Table 1, wherein the sequences are combined 5'3' in the order (i), (ii), and (iii).

8. The recombinant product according to claim 7, wherein the host cells are CHO cells.

9. A recombinant product useful for treating a bleeding disorder, wherein the recombinant product comprises functional human von Willebrand Factor proteins that can be recognized by anti-von Willebrand Factor antibodies and are produced by a recombinant method comprising the steps of
    (1) culturing transformed host mammalian cells from a mammalian cell line, wherein such a transformed host cell comprises an expression vector which comprises
        (a) the von Willebrand Factor-encoding nucleotide sequences of
            (i) pVVVH33 (ATCC No. 53090),
            (ii) pVWH5 (ATCC No. 53088), and
            (iii) the sequence of nucleotides 9 through 587 of Table 1, wherein the sequences are combined 5'3' in the order (i), (ii), and (iii), and
        (b) heterologous DNA effective to cause expression of the von Willebrand Factor-encoding nucleotide sequences, wherein the culturing is performed in a culture medium and under conditions permitting the transformed host cell to express the functional von Willebrand Factor protein, and
    (2) recovering the functional von Willebrand Factor protein.

10. The recombinant product according to claim 9, wherein the host cells are CHO cells.

11. A recombinant product useful for treating a bleeding disorder, wherein the recombinant product comprises functional human von Willebrand Factor proteins that can be recognized by anti-von Willebrand Factor antibodies, and wherein the functional human von Willebrand Factor proteins are produced by a recombinant method comprising the step of
    culturing host cells from a mammalian cell line, wherein such a host cell is transformed with DNA that comprises an open reading frame that is 8 to 9 kb in length and encodes functional human von Willebrand Factor protein that has an amino acid sequence that is set forth in Table 2.

12. The recombinant product according to claim 11, wherein the host cells are COS cells.

13. The recombinant product according to claim 11, wherein the host cells are CHO cells.

14. A recombinant product comprising functional multimers of human von Willebrand Factor protein, wherein the human von Willebrand protein is produced by a recombinant method comprising the step of culturing host cells from a mammalian cell line, wherein such a host cell is transformed with a DNA sequence that comprises an open reading frame that is 8 to 9 kb in length and encodes functional human von Willebrand Factor protein that has an amino acid sequence set forth in Table 2.

15. The recombinant product according to claim 14, wherein the host cells are CHO cells.

16. The recombinant product according to claim 14, wherein the host cells are COS cells.

17. A host cell from a mammalian cell line, wherein the host cell is transformed with a vector for expression of functional human von Willebrand Factor protein that can be recognized by anti-von Willebrand Factor antibodies, wherein the vector comprises
  (a) the von Willebrand Factor-encoding nucleotide sequences of
    (i) pVWH33 (ATCC No. 53090),
    (ii) pVWH5 (ATCC No. 53088), and
    (iii) the sequence of nucleotides 9 through 587 of Table 1, wherein the sequences are combined 5'3' in the order (i), (ii), and (iii), and
  (b) heterologous DNA effective to cause expression of the von Willebrand Factor-encoding nucleotide sequences.

18. A host cell according to claim 17, wherein the combined von Willebrand Factor-encoding nucleotide sequences have a combined nucleotide sequence that is set forth in Table 2.

19. A host cell from a mammalian cell line, wherein the host cell is transformed with an expression vector comprising DNA comprising an open reading frame that is 8 to 9 kb in length and encodes functional human von Willebrand Factor protein that can be recognized by anti-von Willebrand Factor antibodies and has an amino acid sequence that is set forth in Table 2.

20. The host cell according to claim 19, wherein the host cell is selected from the group consisting of a COS cell and a CHO cell.

21. The host cell according to claim 19, wherein the open reading frame comprises 8439 nucleotides.

22. The host cell according to claim 20, wherein the host cell is a CHO cell.

23. An expression vector for transforming a mammalian host cell for expression of functional human von Willebrand Factor protein that can be recognized by anti-von Willebrand Factor antibodies, wherein the vector comprises
  (a) the von Willebrand Factor-encoding nucleotide sequences of
    (i) pVWH33 (ATCC No. 53090),
    (ii) pVWH5 (ATCC No. 53088), and
    (iii) the sequence of nucleotides 9 through 587 of Table 1,
    wherein the sequences are combined 5'3' in the order (i), (ii), and (iii), and
  (b) heterologous DNA effective to cause expression of the von Willebrand Factor-encoding nucleotide sequences.

24. An expression vector according to claim 23, wherein the combined von Willebrand Factor-encoding nucleotide sequences have a combined nucleotide sequence that is set forth in Table 2.

25. An expression vector for transforming a host cell for expression of a functional human von Willebrand Factor protein that can be recognized by anti-von Willebrand Factor antibodies, wherein the expression vector comprises a DNA comprising an open reading frame that is 8 to 9 kb in length and encodes functional human von Willebrand Factor protein having an amino acid sequence that is set forth in Table 2, and wherein the host cell is from a mammalian cell line.

26. The expression vector according to claim 25, wherein the host cell is selected from the group consisting of a COS cell and CHO cell.

27. The expression vector according to claim 25, wherein the open reading frame comprises 8439 nucleotides.

28. The expression vector according to claim 26, wherein the host cell is a CHO cell.

29. An isolated DNA sequence encoding functional human von Willebrand Factor protein that can be recognized by anti-von Willebrand Factor antibodies, wherein the DNA comprises the von Willebrand-encoding nucleotide sequences of
  (i) pVWH33 (ATCC No. 53090),
  (ii) pVWH5 (ATCC No. 53088), and
  (iii) the sequence of nucleotides 9 through 587 of Table 1, wherein the sequences are combined 5'3' in the order (i), (ii), and (iii) wherein the isolated DNA sequence is in a vector.

30. An isolated DNA according to claim 29, wherein the isolated DNA has a nucleotide sequence that is set forth in Table 2.

31. An isolated DNA sequence that has a continuous open reading frame encoding functional human Von Willebrand Factor protein that has an amino acid sequence that is set forth in Table 2, wherein the isolated DNA sequence is in a vector.

32. The isolated DNA sequence according to claim 31, wherein the vector is in a transformed host cell from a mammalian cell line.

33. The isolated DNA sequence according to claim 32, wherein the host cell is a CHO cell.

34. The isolated DNA sequence according to claim 32, wherein the host cell is a COS cell.

35. An isolated DNA sequence comprising an open reading frame that is 8 to 9 kb in length and encodes a functional human von Willebrand Factor protein that can be recognized by anti-von Willebrand Factor antibodies, wherein the isolated DNA is in a vector and the functional human von Willebrand Factor protein has an amino acid sequence that is set forth in Table 2.

36. The isolated DNA according to claim 35, wherein the open reading frame comprises 8439 nucleotides.

* * * * *

UNITED STATES PATENT AND TRADEMARK OFFICE
CERTIFICATE OF CORRECTION

| | | |
|---|---|---|
| PATENT NO. | : 8,597,910 B1 | |
| APPLICATION NO. | : 07/559509 | |
| DATED | : December 3, 2013 | |
| INVENTOR(S) | : David Ginsburg et al. | |

It is certified that error appears in the above-identified patent and that said Letters Patent is hereby corrected as shown below:

On the Title Page, left column, Item (54) and in the Specification, column 1, delete the title and insert the following as the title:

-- DNA ENCODING VON WILLEBRAND FACTOR (VWF) AND METHODS AND CELLS FOR PRODUCING VWF, AND VWF PRODUCED BY THE DNA, METHODS AND CELLS --.

In the Specification

Column 3, line 61, delete "gt1l" and insert -- gt11 --.

Column 3, line 64, delete "ITPG/XGa1" and insert -- ITPG/XGal --.

Column 5/6, Table 1, delete the sequences at lines 28-31 and insert the following sequences:

```
          250         260         270         280         290         300
           *           *           *           *           *           *
--  CAC AAG TGT CTG GCT GAG GGA GGT AAA ATT ATG AAA ATT CCA GGC ACC TGC TGT GAC ACA  --.
     H   K   C   L   A   E   G   G   K   I   M   K   I   P   G   T   C   C   D   T
```

Column 5/6, Table 1, delete the sequences at lines 36-39 and insert the following sequences:

```
          370         380         390         400         410         420
           *           *           *           *           *           *
--  TGT AAG TCT GAA GTA GAG GTG GAT ATC CAC TAC TGC CAG GGC AAA TGT GCC AGC AAA GCC  --.
     C   K   S   E   V   E   V   D   I   H   Y   C   Q   G   K   C   A   S   K   A
```

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,597,910 B1

Column 5/6, Table 1, delete the sequences at lines 44-47 and insert the following sequences:

```
          490        500        510        520        530        540
           *          *          *          *          *          *
 ACG GAG CCC ATG CAG GTG GCC CTG CAC TGC ACC AAT GGC TCT GTT GTG TAC CAT GAG GTT
  T   E   P   M   Q   V   A   L   H   C   T   N   G   S   V   V   Y   H   E   V
--                                          ▲                                   --.
```

In the Claims

Column 8, line 60, delete "ug/ml" and insert -- µg/ml --.

Column 27, line 21, delete "kd." and insert -- kD --.

Column 28, line 63, delete "TON X-100TH" and insert -- TON X-100™ --.

Column 30, line 26, delete "pVVVH33" and insert -- pVWH33 --.